(12) United States Patent
Figulla et al.

(10) Patent No.: US 7,665,466 B2
(45) Date of Patent: Feb. 23, 2010

(54) SELF-EXPANDING MEDICAL OCCLUSION DEVICE

(75) Inventors: Hans Reiner Figulla, Jena (DE); Susann Klebon, Jena (DE); Friedrich Moszner, Hohlstedt (DE); Robert Moszner, Bad Klosterlausnitz (DE); Rudiger Ottma, Grossschwabhausen (DE)

(73) Assignee: Occlutech GmbH, Jena (DE)

( * ) Notice: Subject to any disclaimer, the term of this patent is extended or adjusted under 35 U.S.C. 154(b) by 497 days.

(21) Appl. No.: 11/271,750

(22) Filed: Nov. 14, 2005

(65) Prior Publication Data

US 2007/0167980 A1    Jul. 19, 2007

(51) Int. Cl.
*A61F 6/06*    (2006.01)

(52) U.S. Cl. .................. 128/830; 128/887; 604/28; 604/96.01; 604/101.05; 604/103.07; 604/107; 604/164.13; 604/264; 604/500; 604/509; 604/528; 604/536; 606/7; 606/15; 606/108; 606/139; 606/144; 606/148; 606/159; 606/185; 606/194; 606/200; 606/213

(58) Field of Classification Search ................ 128/830, 128/887; 604/28, 96.01, 101.05, 103.07, 604/107, 164.13, 264, 500, 509, 528, 536; 606/7, 15, 108, 139, 144, 148, 159, 185, 606/194, 200, 213

See application file for complete search history.

(56) References Cited

U.S. PATENT DOCUMENTS

| 5,725,552 | A | 3/1998 | Kotula et al. |
| 6,723,112 | B2 * | 4/2004 | Ho et al. .................... 606/191 |
| 7,128,073 | B1 * | 10/2006 | van der Burg et al. ....... 128/887 |
| 2006/0036045 | A1 * | 2/2006 | Wilson et al. ............... 525/452 |
| 2006/0116712 | A1 * | 6/2006 | Sepetka et al. ............. 606/200 |
| 2006/0247680 | A1 * | 11/2006 | Amplatz et al. ............ 606/213 |
| 2007/0043391 | A1 * | 2/2007 | Moszner et al. ............ 606/213 |
| 2007/0112380 | A1 * | 5/2007 | Figulla et al. .............. 606/213 |

FOREIGN PATENT DOCUMENTS

| DE | 103 38 702 B3 | 3/2005 |
| WO | WO 99/12478 A | 3/1999 |

\* cited by examiner

*Primary Examiner*—Bernard Lipman
(74) *Attorney, Agent, or Firm*—Inskeep IP Group, Inc.

(57) ABSTRACT

A self-expanding medical occlusion device treats a heart defect in a patient and is inserted into the body in minimally invasive fashion using a catheter system, and includes a braiding of thin threads which exhibits a first preliminarily definable shape as the occlusion device is being inserted into the patient's body and a second preliminarily definable shape in the implanted state, whereby the occlusion device is in a collapsed state in the first shape of the braiding and in an expanded state in the second shape of the braiding. The threads of braiding are composed of a shape memory polymer composite such that braiding deforms from a temporary shape to a permanent shape in consequence of an external stimulus, whereby the temporary shape is given in a first profile form of the braiding and the permanent shape is given in a second profile form of the braiding.

34 Claims, 25 Drawing Sheets

PFO-occlusion device Type 1

○ Permanent, covalent crosslinking
∽ Flexible, amorphous network segment
— Temporary, physical crosslinking PFO-occlusion device Type 1

PFO-occlusion device Type 1

PFO-occlusion device Type 2

PFO-occlusion device Type 3

PFO-occlusion device Type 4

ASD-occlusion device Type 1

ASD-occlusion device Type 2

ASD-occlusion device Type 3

ASD-occlusion device Type 4

ASD-occlusion device Type 1

ASD-occlusion device Type 2

ASD-occlusion device Type 3

ASD-occlusion device Type 4

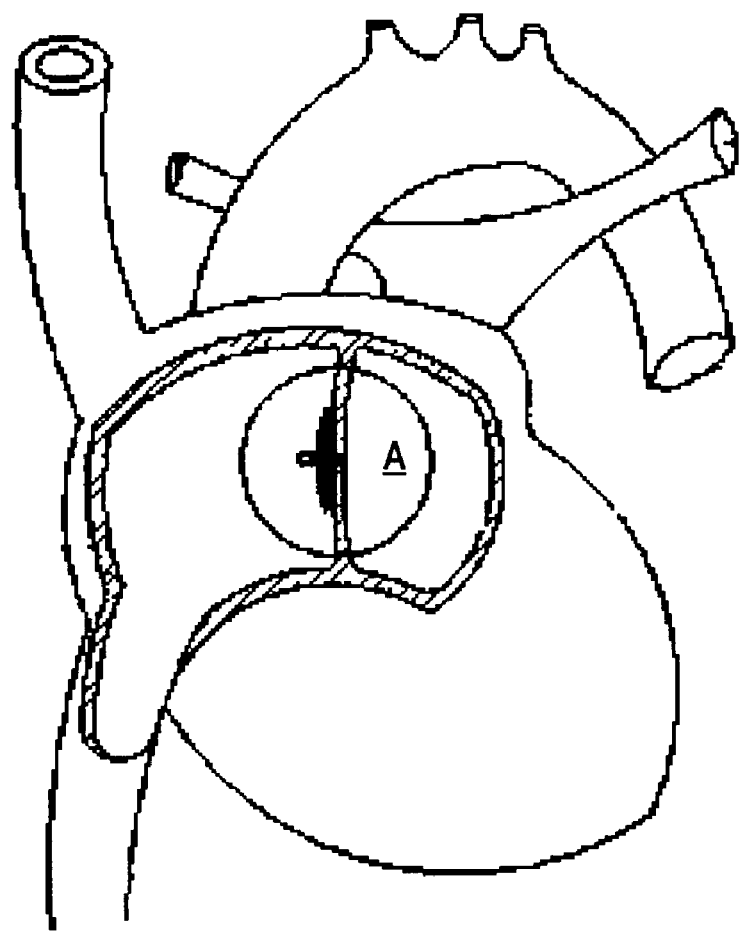
Fig. 23
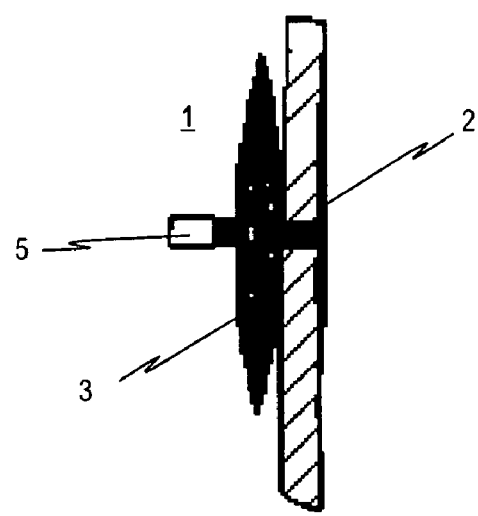
A ( 2 : 1 )

VSD-occlusion device

VSD-occlusion device

VSD-occlusion device

PDA-occlusion device

PDA-occlusion device

SELF-EXPANDING MEDICAL OCCLUSION DEVICE

BACKGROUND OF THE INVENTION

1. Field of the Invention

The present invention relates to a self-expanding medical occlusion device for treating heart defects in patients, in particular closing abnormal openings in tissue, whereby the occlusion device is introduced into the body of a patient in minimally invasive fashion using a catheter system and consists of a braiding of thin threads, whereby the braiding exhibits a first preliminarily definable shape as the occlusion device is being inserted into the patient's body and a second preliminarily definable shape in the implanted state of the occlusion device, whereby the braiding of said occlusion device in the first profile form is in a collapsed state and the braiding in the second profile form is in expanded state.

2. Description of the Related Art

The principle behind this type of occlusion device is known to at least some extent in medical technology. For example, an occlusion device for treating septum defects is known from DE 10 338 702 of Aug. 22, 2003, consisting of a braiding of thin wires or threads and given a suitable profile in a molding and heat treatment process. The known occlusion device has a proximal retention area which is particularly distinctly flat, a distal retention area, and a cylindrical crosspiece between said proximal and distal retention areas. The ends of the wires forming the braiding converge into a holder in the distal retention area. This is hence designed as such so that the two retention areas of the known occlusion device will position on the two sides of a shunt to be occluded in a septum, usually by means of an intravascular surgical procedure, while the crosspiece will transverse the shunt.

Medical technology has long endeavored to be able to occlude septal defects, for instance atrioseptal defects, by means of non-surgical transvenous catheter procedures, in other words, without having to perform an operation in the literal sense. Various different occlusion systems have been proposed, each with their own pros and cons, without any one specific occlusion system having yet become widely accepted.

In making reference to these different systems, the following will use the terms "occluder" or "occlusion device." In all interventional occlusion systems, a self-expanding umbrella system is introduced transvenously into a defect to be occluded in a septum. This type of system might comprise two umbrellas: one, for example, positioned at the distal side of the septum (i.e. the side furthest from the median plane of the body/heart) and one at the proximal side of the septum (i.e. the side closer to the median plane of the body), whereby the two umbrella prostheses are subsequently secured to a double umbrella in the septal defect. Thus, in the assembled state, the occlusion system usually consists of two clamped umbrellas connected to one another by means of a short bolt transversing the defect.

However, a disadvantage to such prior art occlusion devices turns out to be the relatively complicated, difficult and complex implantation procedure. Apart from the complicated implantation of the occlusion system in the septal defect to be occluded, the umbrellas utilized are susceptible to material fatigue along with fragment fracture. Furthermore, thromboembolic complications are frequently to be anticipated.

In order to enable the inventive occlusion device to be introduced by means of a surgical insertion instrument and/or guidewire, a holder is provided at the end of the distal retention area which can engage with the insertion instrument and/or guidewire. It is thereby intended that this engagement can be readily disengaged after positioning the occlusion device in the defect. For example, it is possible to devise the braiding at the end of the distal retention area of the occlusion device in such a manner so as to create an internal threading in the holder to engage with the insertion instrument. Of course, other embodiments are naturally also conceivable.

With another type of occlusion device, the so-called Lock-Clamshell umbrella system, two stainless steel preferably Dacron-covered umbrellas are provided, each stabilized by four arms. This type of occluder is implanted into the patient through a vein. However, seen as problematic with the Lock-Clamshell occluder is the fact that the insertion instruments necessary to implant the device need to be of relatively large size. A further disadvantage seen with other systems, for example the Amplatz occluder, is that many different occluder sizes are needed in order to cope with the respective dimensions of the septal defects to be occluded. It thus turns out that the umbrellas do not flatten out completely in the inserted state if the length or the diameter of the crosspiece inserted into the defect is not of an optimum match. This results in incomplete endothelialization. It has furthermore been shown that many of the systems implanted into patients' bodies exhibit material fatigue and fractures in the metallic structures due to the substantial mechanical stresses over a longer period. This is especially the case given permanent stress between an implant and the septum.

In order to overcome these disadvantages, self-centering occlusion devices have been developed which are inserted into the body of the patient and introduced into the septal defect to be occluded by way of a minimally invasive procedure, for example using a catheter and guidewires. Their design is based on the principle that the occlusion device can be tapered to the dimensions of the insertion instrument and/or catheter used for the intravascular procedure. Such a tapered occlusion device is then introduced by catheter into the septal defect to be occluded, respectively into the shunt of the septum defect to be occluded. The occluder is then discharged from the catheter, upon which the self-expanding umbrellas, retention plates respectively, subsequently unfold against the two sides of the septum. The umbrellas in turn comprise fabric inserts made from or covered by, for example, Dacron, with which the defect/shunt is occluded. The implants remaining in the body are more or less completely ingrown by the body's own tissue after a few weeks or months.

An example of a self-centering occlusion device of the type specified is known from WO 99/12478 A1, which is a further development of the occlusion device known as the "Amplatz occluder" in accordance with US printed U.S. Pat. No. 5,725,552. Same consists of a braiding of a plurality of fine, intertwined nitinol wire strands in the shape of a yo-yo. Each braiding is produced in its original form as a rounded braiding having loose wire ends both at its leading end (its proximal side, respectively) as well as at its trailing end (its distal side, respectively). During the subsequent processing of the rounded braiding, each of these loose ends must then be gathered into a sleeve and welded together. After the appropriate processing, both the proximal side as well as the distal side of the finished occluder exhibit a protruding collar. Dacron patches are sewn into the distal and proximal retention umbrellas and the interposed crosspiece. Because of the memory effect exhibited by the nitinol material used, the two retention umbrellas unfold by themselves upon exiting the catheter, initially in a balloon-like intermediate stage, whereby the retention umbrellas ultimately positioned on the two sides of the septum eventually assume a more or less flattened form. The crosspiece centers itself automatically into the shunt to be occluded during the positioning of the umbrellas.

The shape memory nitinol material known from prior art occlusion devices and that as previously described has, however, proven to have certain disadvantages with respect to occlusion devices. Nitinol, which is an atomistic alloy of nickel and titanium, is only conditionally suitable as a shape memory material for medical occlusion devices because the maximum deformation for nitinol between the first preliminarily definable shape given as the occlusion device is being inserted into the body of the patient and the second preliminarily definable shape given when the occlusion device is in implanted state only amounts to about 8%. In other words, this means that the shape memory nitinol material is only conditionally suitable for collapsing an occlusion device as small as possible for the implantation procedure. Hence, the implantation procedure when using a medical occlusion device which has braiding made from nitinol is not a particularly gentle one on the patient. Moreover, being an alloy of nickel and titanium, nitinol constitutes a permanent foreign body such that once in the implanted state, relevant defense system reactions can be expected from the body.

On the basis of the problematic task as set forth, which is in particular coupled with the use of nitinol as a shape memory material for medical occlusion devices, the task on which the present invention is based is that of improving upon a self-expanding medical occlusion device of the type specified at the outset to afford the patient a gentler implantation of the device.

SUMMARY OF THE INVENTION

This task is solved in accordance with a self-expanding medical occlusion device of the type specified at the outset which inventively has the threads of the braiding including a shape memory polymer composite so that the braiding is deformed from a temporary shape to a permanent shape by means of an external stimulus, whereby the temporary shape is given in a first profile form and the permanent shape is given in a second profile form.

The inventive solution has a number of significant advantages over the known and above-described medical occlusion devices of the prior art. Especially because a shape memory polymer composite exhibits considerably better memory properties than nitinol, a far gentler implantation is afforded when implanting said medical occlusion device. Compared to known shape memory materials, for example the nitinol shape memory alloy; i.e., an atomistic alloy of nickel and titanium, shape memory polymers are far superior in terms of their memory properties. Only little effort is required in the (heating/cooling) process to program the temporary shape or, respectively, to restore the permanent shape. Moreover, in the case of nitinol, for example, the maximum deformation between permanent and temporary shape amounts to just 8%. In contrast, shape memory polymers exhibit substantially higher deformability capabilities of up to 1100%.

The inventive polymer composite also exhibits advantages over the prior art with respect to the manufacturing process since conventional processing methods can be used. For example, the polymer could conceivably be initially given its permanent shape using conventional processing methods such as injection molding or extrusion. The synthetic can then be subsequently deformed and fixed in its desired temporary shape, which is a process known as "programming." This procedure can ensue with polymers such that the specimen is heated, deformed and then cooled. Or the polymer/synthetic can also be deformed at lower temperature, a process known as "cold drawing." The permanent form thus becomes a memory shape which is remembered while still in temporary form. Once an external stimulus acts on the molded polymer body, this leads to the shape memory effect being triggered and thus to a restoring of the permanent memory shape. Cooling the specimen effects an irreversible degeneration of the temporary shape, which is why this is referred to as a so-called one-way shape memory effect. The original temporary form—as well as other forms—can be reprogrammed upon new mechanical deformation being effected.

Shape-memory polymers are included in a group which is known as smart polymers in English and are polymers which exhibit a shape memory effect; i.e., which are able to change their outer form in response to external stimuli such as, for example, a change in temperature. The above-described process of programming and shape restoration is depicted schematically in FIG. 1.

A particularly preferred implementation provides for the external stimulus being a definable switching temperature. It is thus conceivable that in order to trigger the shape memory effect and thus the restoring of the permanent memory shape, the braiding of the molded polymer body must be heated to a higher temperature than the switching temperature. Appropriately selecting the chemical composition to a polymer composite allows the initial specifying of such a specific transition temperature.

It is thus particularly preferred to set the switching temperature within a range of between room temperature and the patient's body temperature. This is of particular advantage as regards the application of the occlusion device as an implant in the body of a patient. As such, all that must be ensured when implanting the occlusion device is that the device is not warmed up to the patient's body temperature (36° C.), which would trigger the polymer's shape memory effect, until in the implanted state.

One possible implementation of the inventive occlusion device in which the external stimulus is a definable switching temperature provides for the polymer composite to comprise polymer switching elements, whereby the temporary shape of the braiding is stabilized below the definable switching temperature based on the characteristic phase transitions of the polymer switching elements.

It is thus conceivable, for example, that should the polymer composite exhibit a crystalline or semi-crystalline polymer network having crystalline switching segments, the temporary shape to the braiding is fixed and stabilized by freezing the crystalline switching segments at crystallization transition, whereby the switching temperature is a function of the crystallization temperature, the switching temperature of the crystalline switching segments respectively.

On the other hand, in the case of a polymer composite such as an amorphous polymer network having amorphous switching segments, it is feasible to fix and stabilize the temporary shape of the braiding at glass transition by freezing of the amorphous switching segments, whereby the switching temperature is a function of the glass transition temperature of the amorphous switching segments.

In accordance with these preferred embodiments, characteristic phase transitions can thus be used to stabilize the temporary shape of the shape memory polymers; i.e., crystallization in the case of crystalline or semi-crystalline polymers and glass transition in the case of amorphous polymers. Accordingly, in the case of elastic polymers composed of covalent bonded polymer networks, the mechanism of shape memory transition is based on the one hand on the stabilizing of the permanent shape by chemical bonding of the polymer chains and, on the other, by the fixing of the temporary form by crystallization of segments (semi-crystalline polymer networks) or by freezing the switching segments in the case of glass transition (amorphous polymer networks). The $T_{trans}$ switching temperature, the exceeding of which triggers the shape memory effect, is accordingly contingent upon the synthetic's $T_m$ melting temperature, the $T_g$ glass transition temperature respectively, in the corresponding temperature range.

FIG. 2 schematically depicts the molecular mechanism of a thermally-induced shape-memory transition for a semi-crystalline polymer network. When the ambient temperature is higher than $T_{trans}$ ($T_m$) of the crystalline switching segments, these segments are then flexible and can be elastically deformed, for example stretched.

The temporary shape which is formed is fixed by cooling below $T_{trans}$ ($T_m$); i.e., by the crystalline areas forming upon cooling, acting quasi as physical crosslinks. When the polymer is heated above $T_{trans}$ ($T_m$), the permanent shape is once again restored. The thermodynamic force driving the resumption of the permanent shape is the entropic gain thereby realized. Amorphous polymer networks having shape memory effect function similar to the semi-crystalline polymer networks having shape memory effect, whereby the switching temperature represents the glass transition temperature and the temporary shape is fixed by freezing the mobility of the amorphous switching segments.

Another advantageous implementation or development of the previously-cited embodiments of the inventive occlusion device provides for the polymer composite to comprise a linear, phase-segregated multiblock copolymer network which can exhibit at least two different phases, whereby the first phase is a hard segment-forming phase in which a plurality of hard segment-forming blocks are formed in the polymer which serve the physical crosslinking of the polymer structure and define and stabilize the permanent shape to the braiding, and whereby the second phase is a switching segment-forming phase, in which a plurality of switching segment-forming blocks are formed in the polymer which serve to fix the temporary shape of the braiding, whereby the transition temperature from the switching segment-forming phase to the hard segment-forming phase is the switching temperature, and whereby conventional methods such as injection molding or extrusion processes can be used to set the profile form to the braiding above the transition temperature of the hard segment-forming phase.

With respect to the chemical composition of the polymer composite of which the braiding of the inventive medical occlusion device is comprised, a preferred implementation of the inventive medical occlusion device having a braiding consisting of a shape memory polymer composite can provide for the polymer composite to have thermoplastic polyurethane elastomers of a multiblock structure, whereby the hard segment-forming phase is formed by conversion of diisocyanates, in particular methylene-bis(4-phenylisocyanate) or hexamethylene diisocyanate, with diols, in particular 1,4-butanediol, and whereby the switching segment-forming phase yields from oligomeric polyether/poly-esterdiols, in particular based on OH-terminated poly(tetrahydrofuran), poly(ϵ-caprolactone), poly(ethylene adipate), poly(ethylene glyocol) or poly(propylenglycol).

In an alternative yet advantageous implementation, it is conceivable for the phase-segregated diblock copolymers of the polymer composite to exhibit an amorphous A-block and a semi-crystallized B-block, whereby the glass transition of the amorphous A-block constitutes the hard segment-forming phase, and whereby the melting temperature of the semi-crystalline B-block serves as the switching temperature for the thermal shape memory effect.

It is advantageously provided in the latter preferred implementation with respect to the polymer composite for this compound to have polystyrol as the amorphous A-block and poly(1,4-butadiene) as the semi-crystalline B-block.

In consequence thereof, the linear phase-segregated multiblock copolymers constitute an important group of shape memory polymers. These polymers have two separate phases, whereby the one phase with the higher transition temperature serves the physical crosslinking and for defining the permanent shape. Conventional processes for profile shaping such as injection molding or extrusion can be used above this melting temperature. As indicated above, the second phase is then molecular switching and serves to fix the temporary shape, whereby the transition temperature of the switching phase ($T_{trans}$) can be a melting or a glass transition temperature.

Included among the shape memory polymers which function in accordance with this operating principle based on linear block copolymers are thermoplastic polyurethane elastomers having a multiblock structure.

As shown in FIGS. 3 and 4, the hard segment-forming phase is usually a process of converting commercial diisocyanates such as, for example, methylene-bis(4-phenyliso-cyanate) (MDI) or hexamethylene diisocyanate (HMDI) with commercial diols such as, for example, 1,4-butanediol. The switching segment-forming phase then yields from the commercially-available oligomeric polyether/polyesterdiols used such as, for example, based on OH-terminated poly(tetrahydro furan), poly(ϵ-caprolactone), poly (ethylene adipate), poly(ethylene glycol) or poly(propylenglycol).

An example yielding from MDI/1,4-butanediol as the hard segment-forming phase and poly(ϵ-caprolactone) is semi-crystalline linear block copolymers having shape memory effect and a switching temperature of $T_m$=44-55° C. at a molecular weight of from 1600 to 8000 g/mol. In contrast thereto, linear shape-memory block copolymers having an amorphous phase and a switching temperature of $T_g$=−5 to 48° C. from MDI/1,4-butanediol as the hard segment-forming phase and flexible poly(ethylene adipate) can have a molecular weight of from 300 to 2000 g/mol.

Alternatively to the embodiment in which the polymer composite, of which the braiding of inventive medical occlusion device is composed, exhibits a phase-segregated diblock copolymer, it is provided for the polymer composite to exhibit a phase-segregated triblock copolymer having a semi-crystalline central B-block and two amorphous terminal A-blocks whereby the A-blocks constitute the hard segment and the B-block establishes the switching temperature.

It would be conceivable here for the polymer composite to have semi-crystalline poly-(tetrahydrofuran) as the central B-block and amorphous poly(2-methyloxazolin) as the terminal A-blocks.

Pursuant thereto, other shape memory polymers based on linear block copolymers and which function according to the above-described operating principle are the claimed phase-segregated diblock or triblock copolymers, which would include, for example, AB-block copolymers of 34 wt. % polystyrol (PS) as the amorphous A-block and 66 wt. % poly(1,4-butadiene) (PB) as the semi-crystallized B-block.

FIG. 5 shows the structure of such diblock or triblock copolymers having shape memory effect. The glass transition of PS is known to be 90° C. and constitutes the hard segment-forming phase. The melting temperature of the PB crystallite serves as the switching temperature for the thermal shape memory effect and is between 45 and 65° C.

Another example likewise shown in FIG. 5 depicts ABA triblock copolymers of semi-crystalline poly(tetrahydrofuran) (PTHF) as the central B-block and amorphous poly(2-methyloxazolin) (POX) as the terminal A-blocks. The A-blocks having an average molecular weight of 1500 g/mol exhibit a glass transition temperature of 80° C. and constitute the hard segment. The B-block having a molecular weight of between 4100 and 18800 g/mol is semi-crystallized and melts between 20 and 40° C. depending upon the molecular weight. The switching temperature can thus vary within this range.

Polymer compounds having polynorbornene, polyethylene/nylon-6-graft copolymers and/or crosslinked poly(ethylene-co-vinyl acetate) copolymers have been determined to be advantageous with respect to the chemical composition of the polymer composite used in the inventive medical occlusion device.

Likewise proven to be advantageous is for the polymer composite to exhibit a covalent crosslinked polymer network formed by polymerization, polycondensation and/or polyaddition of difunctional monomers or macromers with additive of tri or higher functional crosslinking, whereby given an appropriate selection of the monomers, their functionality and ratio of crosslinkers, the chemical, thermal and mechanical properties of the polymer network as formed can be specifically and selectively set. This thus enables the precise and advance establishing of the properties for the occlusion device at the transition from the first preliminary definable profile shape to the second preliminary definable profile shape, and in particular, the precise and advance establishing of the course of events upon expansion of the occlusion device.

A particularly preferred implementation of the latter embodiment provides for the polymer composite to be a covalent polymer network which constitutes a crosslinker by crosslinking copolymerization of stearylacrylate and methacrylic acid with N,N'-methylenebisacrylamide, whereby the shape memory effect of the polymer composite is based on crystallizing stearyl-side chains.

It is likewise feasible for the polymer composite to exhibit a covalent crosslinked polymer network which is formed by subsequent crosslinking of linear or branched polymers.

Additionally conceivable here would be, for example, activating the crosslinking by ionizing radiation or by thermal fission of radical-forming groups.

Hence, a large group of shape-memory polymers constitute the covalent crosslinked polymer networks as previously indicated at the outset. Based on their structure, two different strategies for synthesis are advantageously followed:

Polymerization, polycondensation or polyaddition of difunctional monomers or macromers with additive of tri or higher functional crosslinking. Given the appropriate selection of the monomers, their functionality and the ratio of crosslinkers, the chemical, thermal and mechanical properties of the polymer network as formed can be specifically and selectively set.

A second synthesis variant for covalent shape-memory polymer networks is given by the subsequent crosslinking of linear or branched polymers. Cross-linking density is hereby heavily dependent on the reaction conditions selected. Here, the crosslinking is usually activated by ionizing radiation or by thermal fission of radical-forming groups. For example, polyethylene films receive heat-shrinking properties from irradiating polyethylene with γ-steel or cross-linked polyethylene-polyvinylacetate copolymers obtain shape memory effect by homogenous addition of the dicumylperoxide radical initiator.

FIG. 6 shows feasible monomers for covalent shape memory polymer networks. Here, for example, covalent polymer networks have shape memory effect obtained by crosslinked copolymerization of stearylacrylate STA and methacrylic acid MAA with N,N'-methylene-bisacrylamide MBA as the crosslinker, the shape memory effect of which is based on the crystallizing stearyl-side chains. Based on the relative stearylacrylate ratio, a melting or switching temperature of between 35 and 50° C. results.

It can be established in summary that both basic types of shape memory polymers; i.e., thermoplastic elastomers and covalent polymer networks, differ in their properties, their processing methods and their programming procedures. The thermoplastic elastomers need a minimum part by weight of hard segment-forming polymer chains to ensure the physical crosslinks. In the case of covalent networks, the ratio of hard segment-forming polymer chains can be higher. It is, of course, conceivable for the described shape memory polymers to find potential application across a wide range of technologies, for example with respect to self-repairing auto bodies, switching elements, sensors and right on up to smart packaging.

Of particular interest with respect to the use of medical occlusion devices are implant materials which are synthetically biodegradable. Degradable materials, respectively polymers, have bonds which are fissionable under physiological conditions. Degradable-ness is the term used if a material decomposes from loss of mechanical properties due to or within a biological system. An implant's external form and dimensions may in fact remain intact during the decomposition. What is meant with respect to degradation time, provided no additional quantifying data is given, is the time it takes for the complete loss of mechanical properties. Biostable materials refer to materials which remain stable within biological systems and which degrade at least only partially over the long term.

The present invention provides for medical occlusion devices of the type specified at the outset and in accordance with the previously-cited preferred embodiments to consist of a braiding which is synthesized from a polymer composite comprising at least one bio-degradable material.

A particularly preferred implementation of the latter embodiment provides for the polymer composite to exhibit a hydrolytically degradable polymer, in particular poly(hydroxy carboxylic acids) or the corresponding copolymers. Hydrolytic degradation has the advantage that the rate at which degradation occurs is independent of the site of implantation since water is present throughout the system.

However, making use of enzymatically degradable polymers is also conceivable in another embodiment. Feasible in particular is that the polymer composite exhibit a biodegradable thermoplastic amorphous polyurethane-copolyester polymer network.

Likewise requisite for the chemical composition to the polymer composite for the inventive medical occlusion device is that the polymer composite exhibit a biodegradable elastic polymer network, obtained from crosslinking of oligomer diols with diisocyanate.

Having polymer composites be formed as covalent networks based on oligo(ε-caprolactone)dimethacrylate and butylacrylate is a conceivable alternative thereto.

For the braiding from which the inventive occlusion device is configured, the invention claims both hydrolytically as well as enzymatically degradable polymer composites for the degradable polymers. As stated above, hydrolytic degradation has the advantage that the rate at which degradation occurs is independent of implant location. In contrast, local enzyme concentrations vary greatly. Given biodegradable polymers or materials, degradation can thus occur through pure hydrolysis, enzymatically-induced reactions or through a combination thereof.

Typical hydrolyzable chemical bonds for the polymer composites of the occlusion device are amide, ester or acetal bonds. Two mechanisms can be noted with respect to the actual degradation. With surface degradation, the hydrolysis of chemical bonds transpires exclusively at the surface. Because of the hydrophobic character, polymer degradation is faster than the water diffusion within the material. This mechanism is seen especially with poly(anhydrides) and poly (orthoesters).

As relates to the poly(hydroxy carboxylic acids) particularly significant especially to the present invention such as poly(lactic acid) or poly(glycol acid), the corresponding copolymers respectively, polymer degradation transpires throughout the entire volume. The step which determines the rate here is the hydrolytic fission of the bonds since water diffusion in the somewhat hydrophilic polymer matrix occurs at a relatively fast rate.

Decisive for the use of biodegradable polymers is that, on the one hand, they degrade at a controlled or variable speed and, on the other, that the products of decomposition are non-toxic.

The concept of polymer material resorption refers to the substance or mass degrading through to the complete removal of a material from the body by way of the natural metabolism. In the case of homogenous implants (occlusion devices) of only one degradable polymer, resorption begins as of that point in time of the complete loss of the mechanical properties. Specification of the resorption time covers the period starting from implantation and running through to the complete elimination of the implant.

Among the most important biodegradable synthetic classes of polymers from which the braiding of the inventive occlusion device is advantageously synthesized are:

polyesters such as poly(lactic acid) PLA, poly(glycol acid) PGA, poly(3-hydroxybutyric acid) PBA, poly(4-hydroxyvalerate acid) PVA or poly($\epsilon$-caprolactone) PCL or the respective copolymers;

polyanhydrides synthesized from dicarboxylic acids such as, for example, glutar PAG, amber PAB or sebacic acid PAS;

poly(amino acids) or polyamides such as, for example, poly(serine ester) PSE or poly(aspartic acid) PAA (FIG. 9).

FIG. 7 shows examples of biodegradable polyesters while FIG. 8 shows examples of biodegradable polyanhydrides, poly(amino acids) and polyamides.

In summary, it can be stated that shape memory properties play a significant role with respect to implants, particularly in terms of minimally invasive medicine. Degradable implants having shape memory properties are particularly effective in this regard.

For example, this type of degradable implant can be introduced into the body in compressed (temporary) form through a small incision and once in place, then assume the memory shape relevant to its application after being warmed by the body temperature. The implant will then degrade after a given interval of time, thereby doing away with the need for a second operation to remove it.

Based on the known biodegradable polymers, structural elements can be derived for the synthesizing of biodegradable shape memory polymers. In so doing, suitable crosslinks, which fix the permanent form, and network chains, which serve as switching elements, must be selected such that, on the on hand, the switching temperature can be realized through the physiological conditions, and on the other, toxicological problems with respect to any products of decomposition are excluded. Thus, suitable switching segments for biodegradable shape memory polymers can be selected based on the thermal properties of known degradable implant material. Of particular interest in this regard is a thermal transition of the switching elements in the temperature range of between room temperature and body temperature. For this transition temperature range, biodegradable polymer segments can be selectively synthesized by varying the stochiometric relationship of the known starting monomers and the molecular weight of the formed polymers in the range of from approx. 500 to 10000 g/mol.

Suitable polymer segments are e.g. poly($\epsilon$-caprolactone) diols with melting temperatures between 46 and 64° C. or amorphous copolyesters based on lactic and glycol acid with glass transition temperatures between 35 and 50° C. The phase transition temperatures hereby; i.e., the melting or glass transition temperature of the polymer switching segments, can be further diminished by their chain length or by degradation of specific end groups. The polymer switching elements thus customized can then be integrated into physical or covalent crosslinked polymer networks, yielding the selectively composed biodegradable shape-memory polymer material.

In one possible embodiment, biodegradable thermoplastic amorphous polyurethane copolyester polymer networks having shape memory properties are used as the material for the inventive occlusion device. First, suitable biodegradable star-shaped copolyester polyols are synthesized here based on commercially available dilactide DL (cyclic lactic acid dimer), diglyocolide DG (cyclic glycol acid dimer) and trimethylolpropane TP (functionality F=3) or pentaerythrit PE (F=4) with glass transition temperatures between 36 and 59° C., which are then crosslinked with commercial trimethylhexa-methylene diisocyanate TMDI in forming a biodegradable polyurethane network.

FIG. 9 shows an example of monomer components for amorphous polyurethane copolyester polymer networks having shape memory properties.

The amorphous polyurethane copolyester polymer networks having shape memory properties as formed have a glass transition temperature $T_g$ between 48 and 66° C. and exhibit a modulus of elasticity in extension of between 330 and 600 MPa, a tensile strength respectively of between 18.3 and 34.7 MPa. Heating these networks to approximately 20° C. above this switching temperature yields elastic materials which can be deformed 50-265% into a temporary shape. Cooling down to room temperature occasions the forming of deformed shape memory polymer networks which have a clearly higher modulus of elasticity in extension of from 770 to 5890 MPa. Upon subsequent reheating to 70° C., the examples of deformed specimens thereby produced retransform back into the permanent corkscrew-like shape after approx. 300 s. What was ultimately shown was that polyurethane copolyester polymer networks in an aqueous phosphate buffer decomposed fully at 37° C. over a period of between approximately 80 and 150 days.

By optimizing the composition of the biodegradable switching segments, degradable polyurethane copolyester polymer networks having shape memory properties can be produced substantially faster, e.g. within 14 days.

Similar biodegradable elastic shape memory polymer networks can be yielded from crosslinking of oligomer diols with diisocyanate TMDI which have melting temperatures between 38 and 85° C. and which are likewise suitable for the inventive occlusion device. Using these materials, a fiber was synthesized and stretched 200% into a temporarily longer fiber and a loose knot formed therefrom. After fixing the two ends of the knot and heating the knot to 40° C.; i.e., higher than the switching temperature, the knot tightened itself again after approx. 20 s into the semi-permanent length through the transition of the thread. Degradableness was also ultimately assessed, whereby for these polymers in an aqueous phosphate buffer at 37° C., a 50% loss of mass was seen after approximately 250 days.

In one possible realization of the inventive occlusion device, the braiding is formed from a biodegradable shape memory polymer on covalent networks based on oligo(ε-capro-lactone)dimethacrylate and butylacrylate. It has been seen that subsequent subcutaneous implantation, this polymer composite has no negative impacts on the wound healing process. The synthesis of such biodegradable shape memory polymers can follow from n-butylacrylate which, because of the low glass transition temperature of −55° C. for pure poly (n-butylacrylate), can be used as the soft segment-forming component.

FIG. 10 shows monomer components for covalent biodegradable networks. The bio-degradable segments are introduced here via the oligo(ε-caprolactone)dimethacrylate crosslinker. Network synthesis ensues through photopolymerization. Based on the molar mass of the macromolecular oligo(ε-caprolactone)dimethacrylate and the content of comonomer n-butylacrylate, the switching temperature and the mechanical properties of the covalent network can be controlled. Thus in an implementation of the inventive solution, the molar mass of the oligo(ε-caprolactone)dimethacrylate varies between 2000 and 10000 g/mol and the n-butylacrylate content between 11 and 90 mass %. In the case of a polymer network based on a mixture of the low molecular oligo(ε-caprolactone)-dimethacrylate at 11 mass % of n-butylacrylate, a melting point of 25° C. was realized.

The biodegradable covalent and physical polymer networks having shape memory effect as described above can also be used as a matrix for a controlled active substance release. Yet also conceivable would be biodegradable polyurethane multiblock copolymers having shape memory effect based on poly(p-dioxanone) PDO as the hard segment and TMDI as the diisocyanate.

FIG. 11 shows polymer segments in biodegradable poly(p-dioxanone)-polyurethane multi-block copolymers. The combination with the poly(lactid-co-glycolid) PDLG or poly(ε-caprolactone) PCL switching segments yields multiblock copolymers having a switching temperature of 37 or 42° C. respectively. The hydrolytic degrading of the polymers shows that the polymers based on PCL degrading at a lesser rate. In a trial on the PCL polymers, 50 to 90% of the initial mass was still present after 266 days of hydrolysis while in the case of the PDLG polymers, 14 to 26% was detectable after only just 210 days.

It can be maintained that biodegradable shape memory polymer networks can be synthesized from a combination of physical or covalent shape memory polymer networks having biodegradable polymer segments. Selectively choosing the components allows setting optimal parameters for each respective application such as the mechanical properties, the deformability, the phase transition temperatures and, above all, the switching temperature, as well as the rate of polymer decomposition.

With respect to the profile form to the inventive medical occlusion device, it is advantageously provided for the second preliminarily definable shape of the occlusion device to be configured to close an abnormal tissue opening in a patient's heart, whereby in its expanded state, the occlusion device exhibits a proximal retention area, a distal retention area and a center section between the two, and in which the occlusion device exhibits a smaller diameter at the center segment than at the proximal and/or distal retention areas. The advantage to this embodiment is in particular seen in that an intravascular occlusion device is provided which is particularly applicable to treating septal defects, patent foramen ovale defects and persistent ductus arteriosus defects and in which the occlusion device can be introduced to the defect to be occluded by means of a catheter system.

Septal defects refer to atrial septal defects (ASD); i.e., a hole in the heart's interatrial partition, and ventricular septal defects (VSD); i.e., a hole in the interventricular partition.

A patent foramen ovale defect (PFO) is an oval opening (slit) in the interatrial partition of the heart which is normally closed after birth by adhesion of the flap-like edges, although imperfect adhesion (persistence) occurs in approximately 25% of all births, leaving an open foramen oval.

The term "persistent ductus arteriosus defect" (PDA) refers to an open passageway between the aorta and the pulmonary artery, one which normally closes after birth.

The main objective of the present invention is to provide a reliable, simple occluding device to be used in the heart which is configured so as to be able to treat patent foramen oval defects (PFO), atrial septal defects (ASD), ventricular septal defects (VSD) and patent ductus arteriosus (PDA) and to do so in a form in which the braiding—as already described above—is replaced by that of a shape memory polymer or biologically degradable shape memory polymer.

In configuring the second preliminarily definable shape to the medical occlusion device from the braiding composed of a polymer, there is a plurality of flexible strands or threads, whereby the threads are braided in such a way so as to produce an elastic material. This braided fabric is then deformed so that it will conform to the outer surface of a molding element. The braided fabric is positioned on the surface of the molding element and subject to thermal treatment at increased temperature. The duration and temperature for the thermal treatment is selected so as to retain the deformation to the braided fabric. Subsequent the thermal treatment, the braided fabric is removed from the molding element, retaining its deformation. A braided fabric treated in this way corresponds to the second preliminarily defined (expanded) shape to the medical occlusion device which can be introduced into a channel in the patient in collapsed state by means of a catheter system.

Types of application for the present invention include special shapes for medical devices, which can then be made in accordance with the present invention in order to be used in specific medical cases. The devices, having a flat expanded shape and which can be disposed with collapsed clamps, can be attached to an end of the insertion device or guidewire in order to retract the device after positioning. In use, a catheter is introduced into the body of the patient to the point where the distal end of the catheter positions exactly at the location which is in need of physiological treatment. A medical device previously selected in accordance with the present invention is then collapsed into a preliminarily defined second shape and inserted into the catheter opening. The device is pushed through the catheter and exits again at its distal end where, due to its memory properties, springs back into its original shape next to the site to be treated. The guidewire or inserting catheter then releases from the clamp and is retracted.

In its second preliminarily defined shape, the occlusion device preferentially exhibits an oblong shape with a tube as its center section and an expanded diameter segment at each end of said center section. The thickness to the center section corresponds roughly to the wall thickness of the organ to be occluded, for example the thickness of the septum.

The center of at least one expanded diameter segment (proximal or distal retention area), can be offset relative the center of the center section. A membranous ventricular septal defect can thus be closed with simultaneous application of a support device large enough to reliably close the abnormal opening of the septum. Each braided end of the device is held by a clamp. These clamps are retracted in the expanded diameter parts of the device, whereby the overall length of the device is reduced and a more flush closure mechanism is yielded.

In another type of application, the device takes on the appearance of a bell having an oblong body with a tapered and a larger endpiece. The larger end has a fabric plate which upon unfolding, positions generally perpendicular the axis of the channel in which the device unfolds. The clamps holding the braided ends together retract into the center of the "bell" and thus yield a flush device having lower overall height.

Since the proximal retention area of the braiding exhibits a flaring toward the proximal end of the occlusion device in a particularly preferred embodiment, this allows for the occlusion device to adjust automatically to the septal defect in particularly advantageous manner—independent of the relative diameter of the defect to be occluded and independent of the thickness of the septal wall—and to do so with no part of the occlusion device projecting beyond the plane of the septal wall with the defect at the proximal side of the defect. There is thus no occurrence of the usual complications which normally arise in such cases. To emphasize, this means that the occlusion device used is ingrown by the body's own tissue substantially faster than is the case with the occluding systems known in the prior art. Using a braiding composed of thin threads as the starting material for the inventive occlusion device yields the further advantage of long-term mechanical stability. This thus largely prevents structural fractures in the inserted implant. In addition, the braiding is afforded sufficient rigidity. The flaring to the proximal end of the braiding's proximal retention area additionally allows the proximal retention area of the device to flatten completely against the lateral edge of the defect in the inserted state and to do so virtually independently of the diameter to the defect or the thickness of the septal wall. As a result, the occlusion device can be used for a wide range of differently sized septal defects. Because there is thus no need for a holder for the bundled or merging braiding at the proximal retention area, neither do any components of the occlusion device protrude past the septum wall, which prevents components of the implant from being in constant contact with the blood. This yields the advantage of there being no threat that the body will mount defense mechanism reactions or of there being thrombembolic complications.

A particular preferred embodiment provides for the center of the proximal/distal retention area to be offset relative the center of the center segment. By so doing, a membranous ventricular septal defect can be occluded and, at the same time, a support device can be used which is large enough to close the abnormal opening in the septum.

Thereto, it can be provided that each braided end of the occlusion device be held by a clamp. These clamps are withdrawn from the occlusion device's expanded diameter parts (proximal and distal retention areas), yielding a reduced overall length to the occlusion device and a more flush closure mechanism.

One advantageous embodiment provides for the interior of the proximal and/or distal retention area to exhibit a concave profile form in the second preliminarily definable shape of the occlusion device in the expanded state. This allows the expanded occlusion device to attain an especially good positioning in the defect to be occluded. It is particularly preferred for the braiding from which the occlusion device is produced to be tapered in a first preliminarily definable shape to the diameter of the catheter system used in the intravascular procedure. This thus enables the occlusion device for occluding a defect to be inserted with a catheter introduced, for example, through a vein, eliminating the need for an operation in the actual sense. When the braiding includes a shape-memory polymer material, as described above, the occlusion device tapered to the diameter of the catheter is known as a "self-expanding device" which unfolds automatically upon exiting the catheter such that the two retention areas can position accordingly at the proximal/distal sides of the defect. The design to the contiguous braiding of the inventive occlusion device moreover occasions an occlusion device which is a self-expanding and self-positioning occluding system which prevents permanent mechanical stress from occurring between the inserted occlusion device and the septum wall. Provided as a conceivable implementation is that the proximal retention area of the braiding exhibit a bell-shaped flaring toward the proximal end.

It would furthermore be conceivable for the proximal retention area to exhibit a bell-shaped flaring to the proximal end. This would thus allow the occlusion device to be used in the treatment of various different defects, in particular ventricular septal defects (VSD), atrioseptal defects (ASD) as well as persistent ductus arteriosus Botalli (PDA), whereby an optimized contouring to the proximal retention area can in principle be selected for a plurality of defects of differing sizes and types. Of course, other profiles are also conceivable in this regard such as, for example, a barbell-like shape. In order to enable a particularly good positioning of the expanded occlusion device at the retention area, it is advantageously provided for the length of the center section to be dimensioned such that the peripheral edge of the distal or proximal retention area overlaps the peripheral edge of the other retention area.

A particularly preferred embodiment of the inventive occlusion device provides for the proximal and/or distal retention area to exhibit a recess in which the holder for bundling the ends of the braiding is disposed. By arranging the holder in the recess provided at the proximal or distal end of the occlusion device, no components of the occlusion device will protrude beyond the septum wall, preventing the components of the implant from coming into constant contact with the blood. This has the advantage of there being no threat that the body will mount defense mechanism reactions or of there being thrombembolic complications. Especially because the expanded occlusion device positions and fixes itself in the defect with the distal and proximal retention areas being radially stressed, the occlusion device can be used for a wide range of defects of various hole sizes.

A particularly preferred embodiment of the inventive occlusion device in which the distal retention area exhibits a recess further provides for the distal end of the occlusion device to be further disposed with a connective element in the recess, whereby said connective element can engage with a catheter. This connective element, which is arranged on the occlusion device so as not to protrude beyond the septum wall such that no components of the implant come into constant contact with the blood, provides the inventive occlusion device with the added functionality of retrievability. Moreover, a connective element which can engage with a catheter facilitates implantation and positioning of the occlusion device (collapsed during the actual implanting) in the defect to be occluded. Various devices are conceivable as connective elements. For example, latching members would be feasible, as would even be hooks/eyelets which force-fit with the correspondingly configured complementary connective elements of a catheter.

Another advantageous embodiment provides for the occlusion device to be configured so as to be reversibly collapsible inward and outward so that the device can be collapsed in its expanded state, for example with the help of an explantation catheter. In conjunction hereto, it is conceivable for a catheter in the explantation procedure to, for example, engage with connective elements configured at the distal end of the occlusion device and occasion the collapsing of the occlusion device in response to external manipulation of the catheter. The occlusion device is thereby fully reversibly retractable in the catheter, enabling the complete removal of the device.

Last but not least, it is particularly preferred for the occlusion device to have at least one fabric insert disposed in or on the distal retention area or in the center section of the occlusion device to occasion complete closure of a defect. This fabric insert serves to close the gaps which remain in the center section and in the expanding diameters of the occlusion device following insertion and expansion of the device in the defect to be occluded. The fabric insert is, for example, affixed to the braiding of the occlusion device at the distal retention area such that it can be stretched over the distal retention area like a cloth. The advantage to this design lies in the fact that the lateral edge of the distal retention area is flush with the septum and less foreign material is introduced into the body of the patient. The fabric inserts can be made of, for example, Dacron. Other materials and other positionings to the fabric insert in or on the occlusion device are of course also conceivable here.

There has thus been outlined, rather broadly, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

The following will make reference to the drawings in providing a more precise detailing of preferred embodiments of the inventive occlusion device.

FIG. 23 depicts a detailed view of a section as seen through the side of an ASD occlusion device pursuant FIG. 21 in the ASD of a heart;

DESCRIPTION OF THE INVENTION

The present invention relates to a percutaneous catheter-guided occlusion device which serves to close abnormal openings such as, for example, atrial septal defects (ASD, PFO), ventricular septal defects (VSD), patent ductus arteriosus (PDA) and the like. The present invention furthermore provides for a method of forming a medical device from a flat or tubular synthetic or polymer fabric. Both the flat as well as the tubular fabric is comprised of a plurality of wire strands having a predefined relative arrangement to one another. The tubular fabric has synthetic strands distinguishing two sets of essentially parallel spiral strands, whereby the strands of one set have a rotation direction counter to that of the other strands. This fabric is also known in the industry as a tubular braid.

Figure 14:
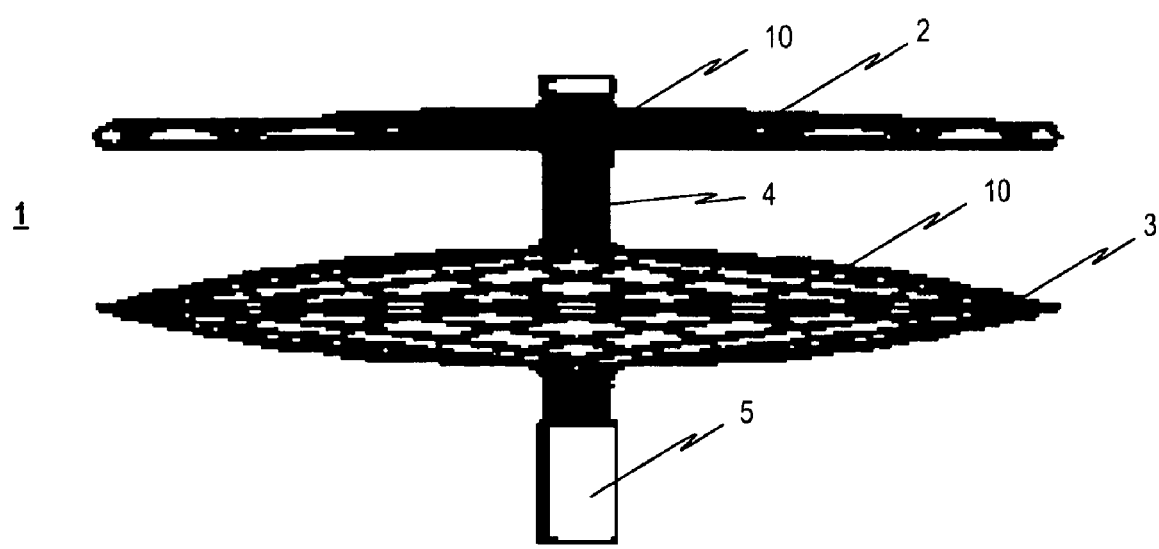
FIG. 14 depicts a side view of a Type 2 PFO occlusion device.
Figure 15:
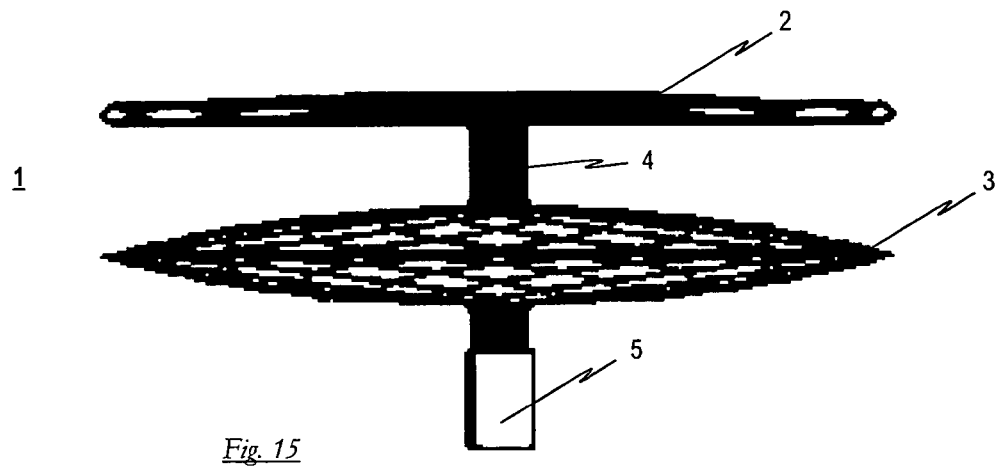
FIG. 15 depicts a side view of a Type 3 PFO occlusion device.
Figure 16:
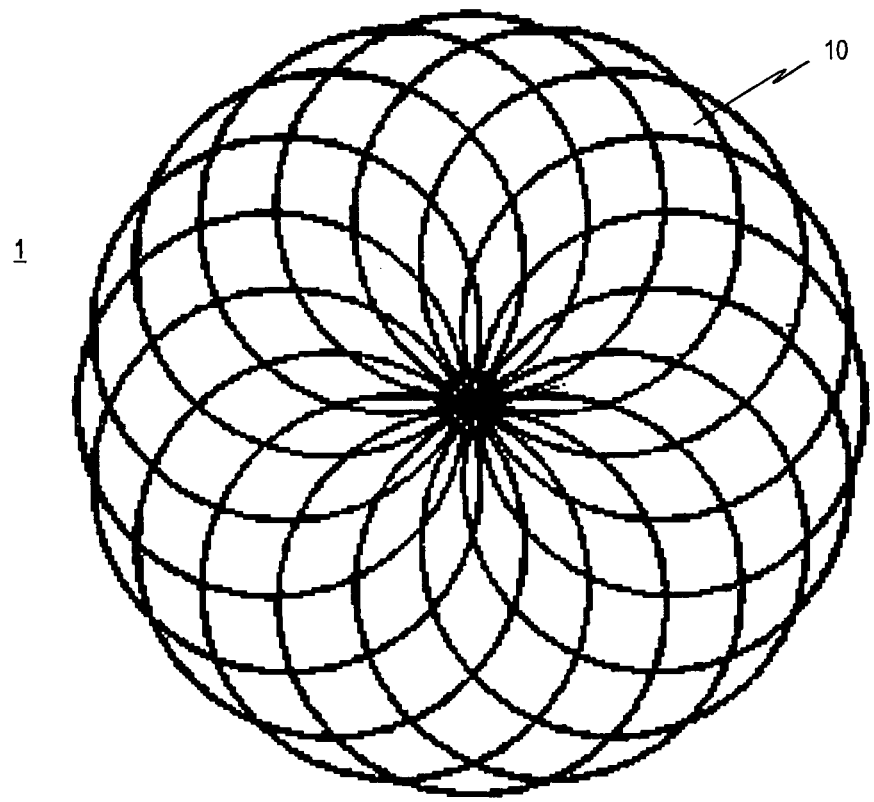
FIG. 16 depicts a top plan view of a Type 3 PFO occlusion device.

The braided form is used primarily in Type 2 (FIG. 14) and Type 3 (FIG. 15) PFO devices, whereby the wires/threads of the proximal curves are thermally bundled at proximal end 2 and specifically in an element which is designated as a "thermal holder." Thermal energy acts here to fuse the wires together.

Figure 24:
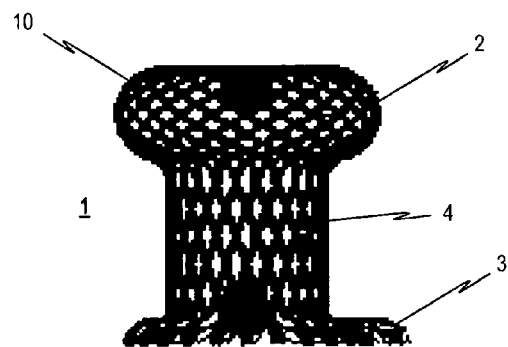
FIG. 24 depicts an enlarged frontal view of an occlusion device for occluding a VSD in its pre-formed shape.
Figure 25:
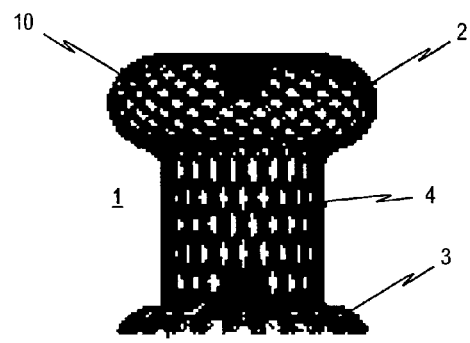
FIG. 25 depicts a side view of the VSD occlusion device pursuant FIG. 24.
Figure 26:
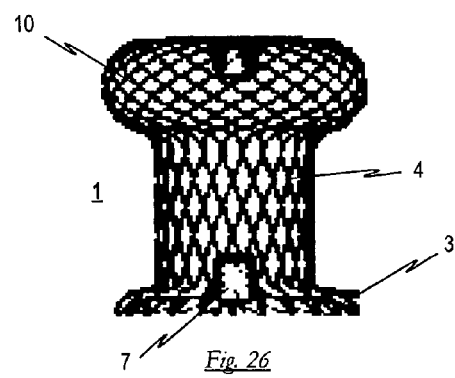
FIG. 26 depicts a detail view of a section as seen through the front of the VSD occlusion device pursuant FIG. 24.
Figure 27:
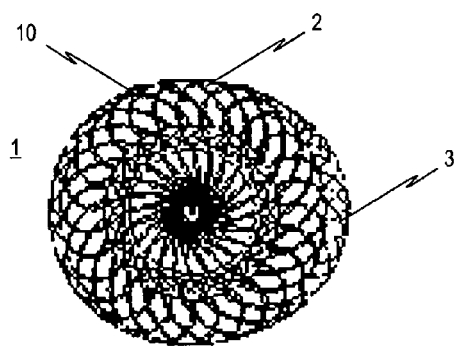
FIG. 27 depicts a surface depiction from above of the VSD occlusion device pursuant FIG. 24.
Figure 28:
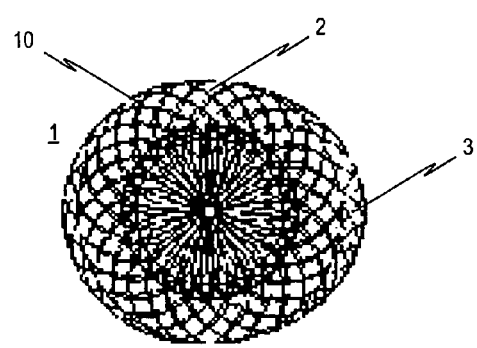
FIG. 28 depicts a surface depiction from below of the VSD occlusion device pursuant FIG. 24.
Figure 35:
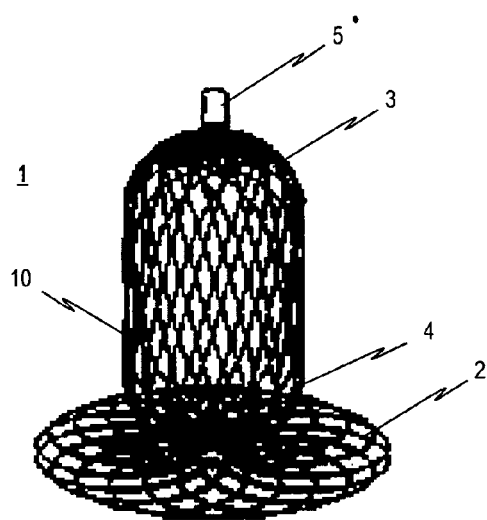
FIG. 35 depicts a perspective view of a medical occlusion device in accordance with the present invention.
Figure 39:
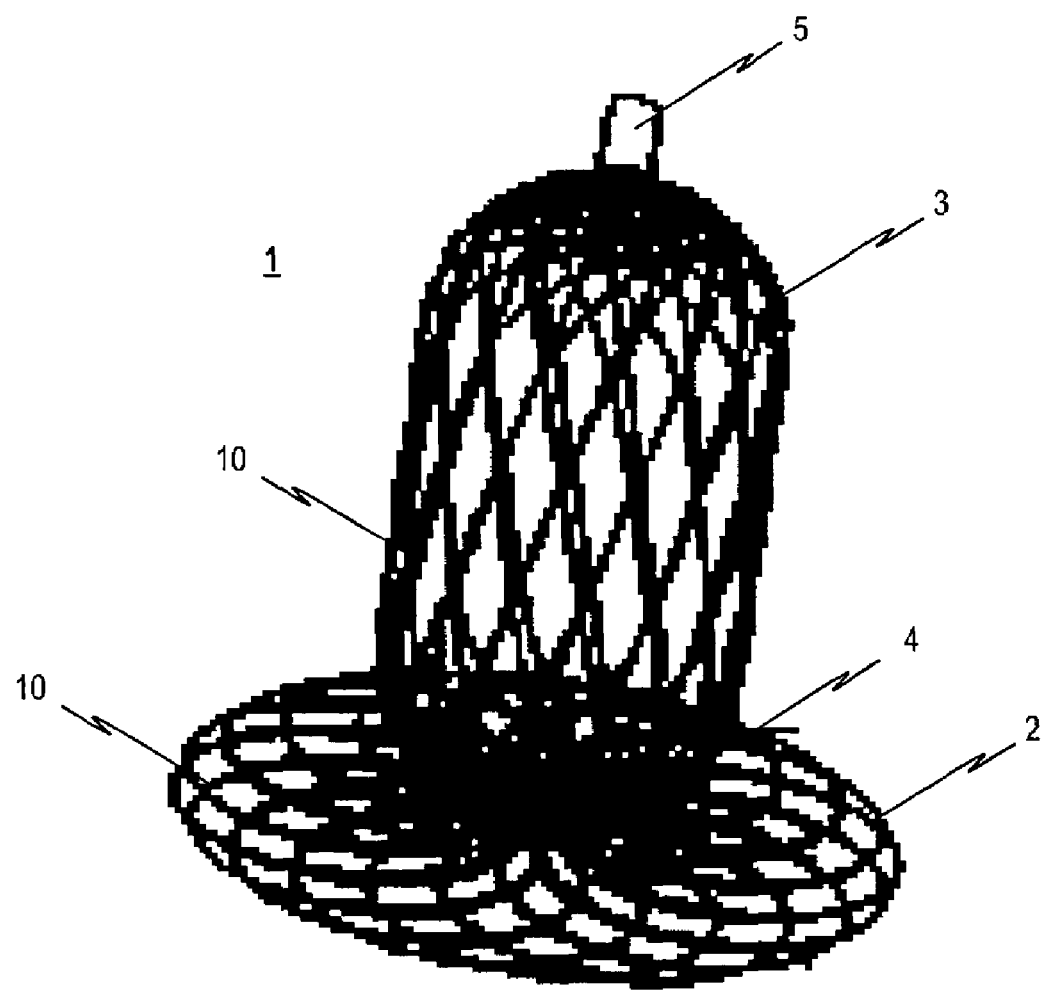
FIG. 39 depicts a perspective view of a medical occlusion device in accordance with the present invention without the associated sleeve in the proximal area as in the occlusion device pursuant FIG. 35.
Figures 41, 42:
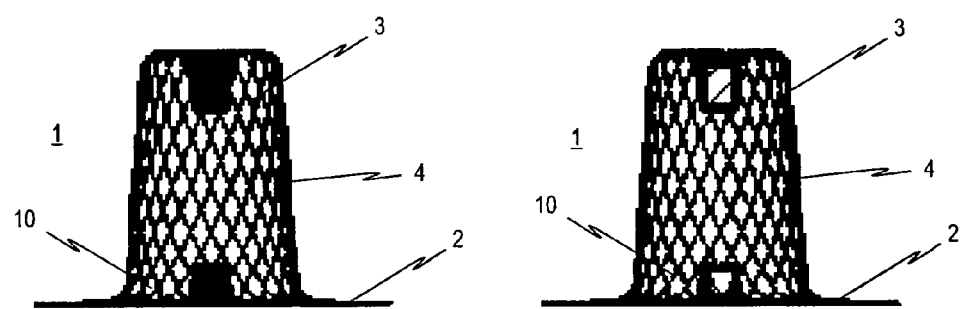
FIG. 41 depicts an enlarged frontal view of an occlusion device used in the occluding of a PDA.
FIG. 42 depicts a detail view of a section through the PDA occlusion device pursuant FIG. 41.
Figures 43, 44:
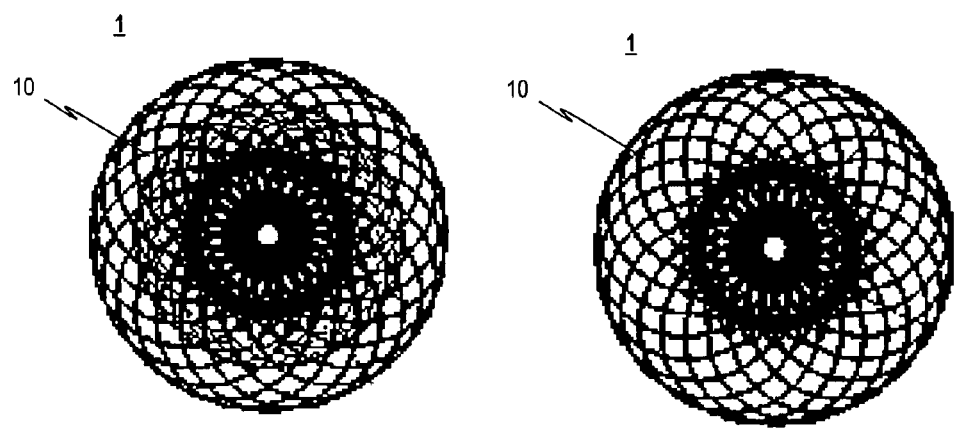
FIG. 43 depicts a top plan view of the PDA occlusion device pursuant FIG. 41.
FIG. 44 depicts a plan view from below of the PDA occlusion device pursuant FIG. 41.

The tubular fabric 10 is used in comparable manner in the Type 2 ASD (FIG. 18b, and FIG. 20a-20c) and Type 3 devices (FIG. 18c, FIG. 21a-21c) in addition to the VSD types of devices (FIG. 24, FIG. 25, FIG. 26), the type of device in accordance with FIGS. 35 and 39, and last but not least, the PDA device in accordance with FIG. 41.

Figure 1:
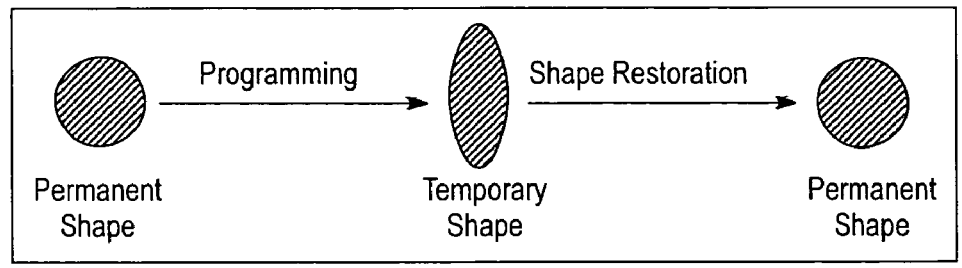
FIG. 1 is a schematic representation of the shape memory effect.
Figure 2:
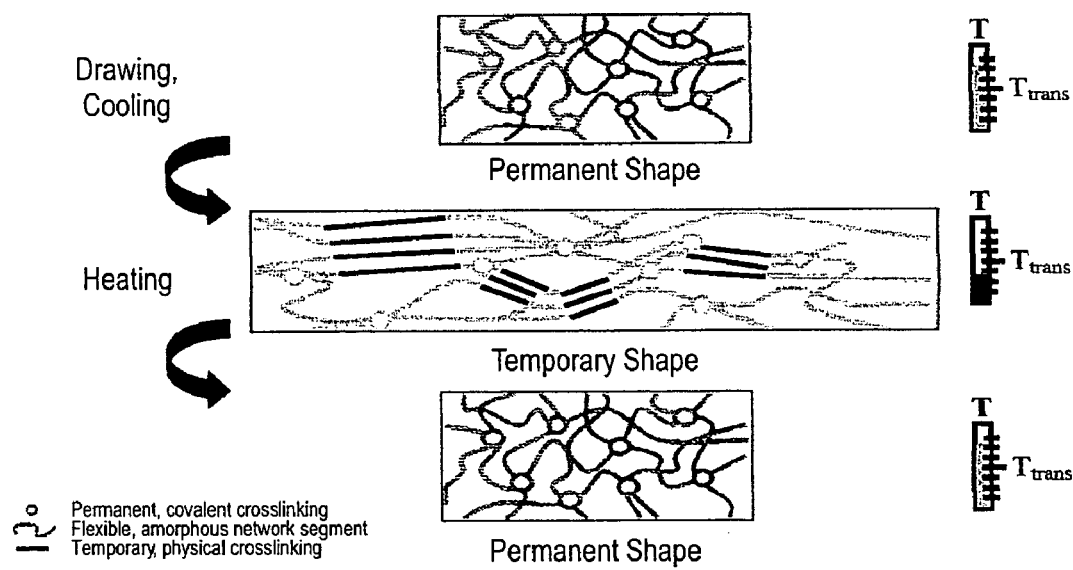
FIG. 2 is a schematic representation of the molecular mechanisms which occur upon shape-memory transition of a semi-crystalline polymer network.
Figure 3:
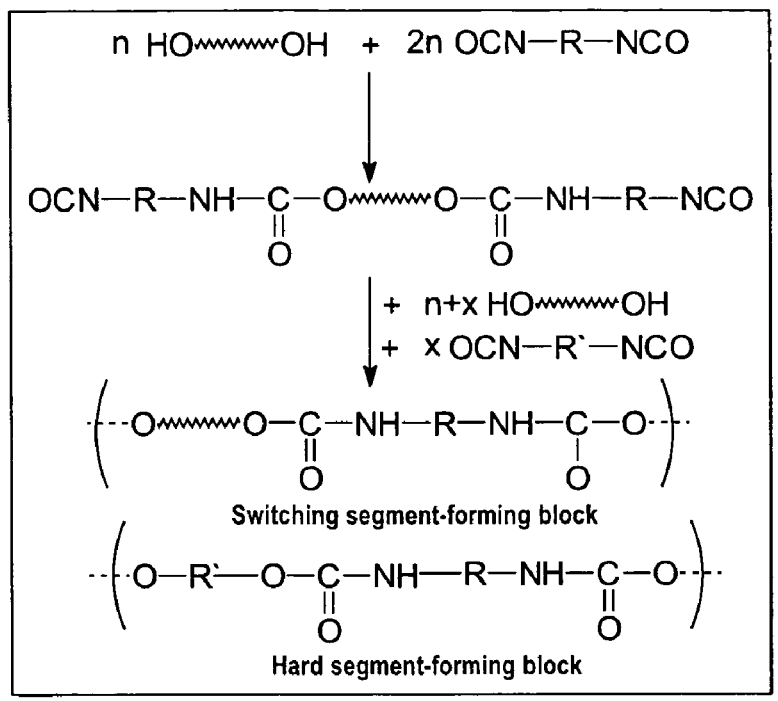
FIG. 3 depicts a synthesis diagram of thermoplastic polyurethane multiblock copolymers.
Figure 4:
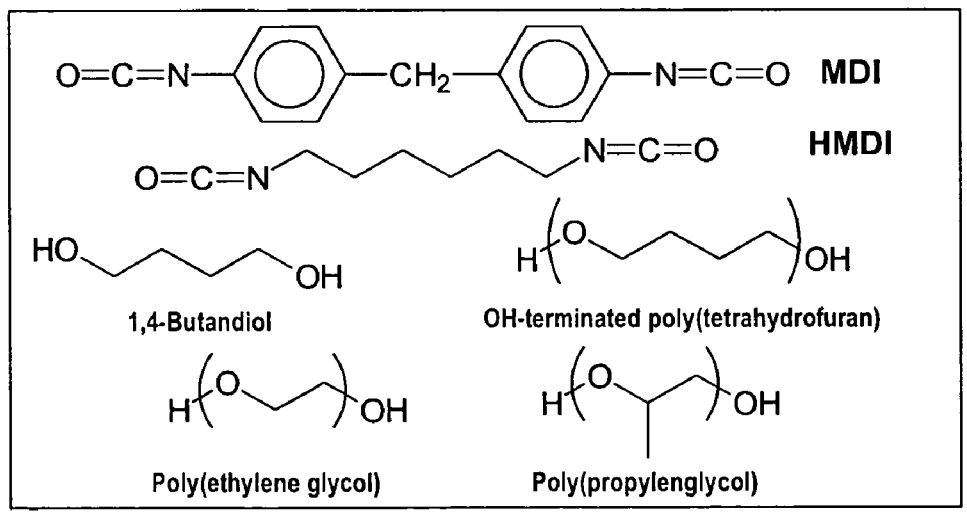
FIG. 4 depicts the chemical structure to monomer components of thermoplastic polyurethane multiblock copolymers.
Figure 5:
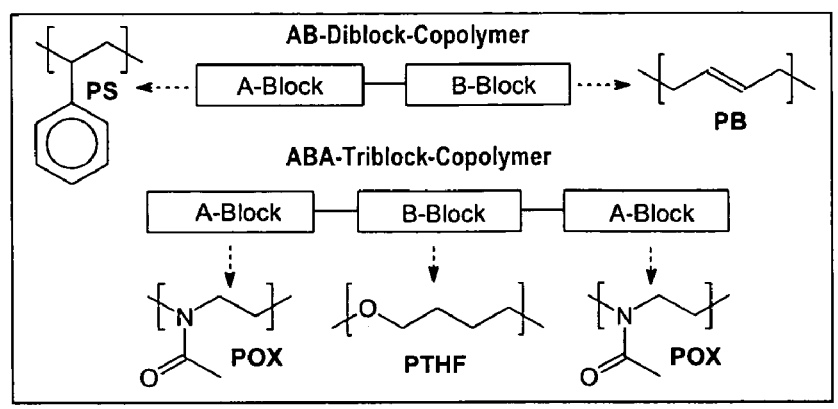
FIG. 5 depicts the structure to diblock or triblock copolymers having shape-memory effect.
Figure 6:
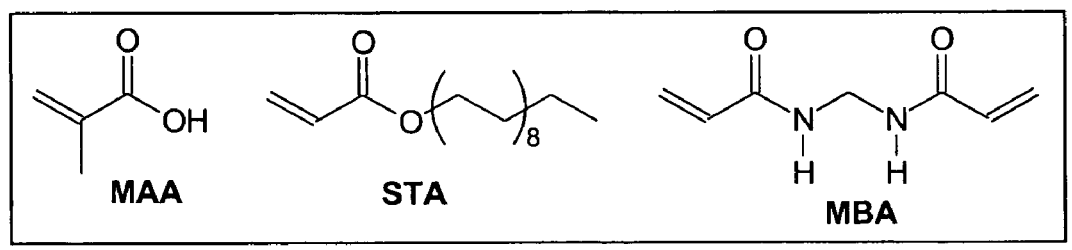
FIG. 6 is a representation of monomers for covalent shape memory polymer networks.
Figure 7:
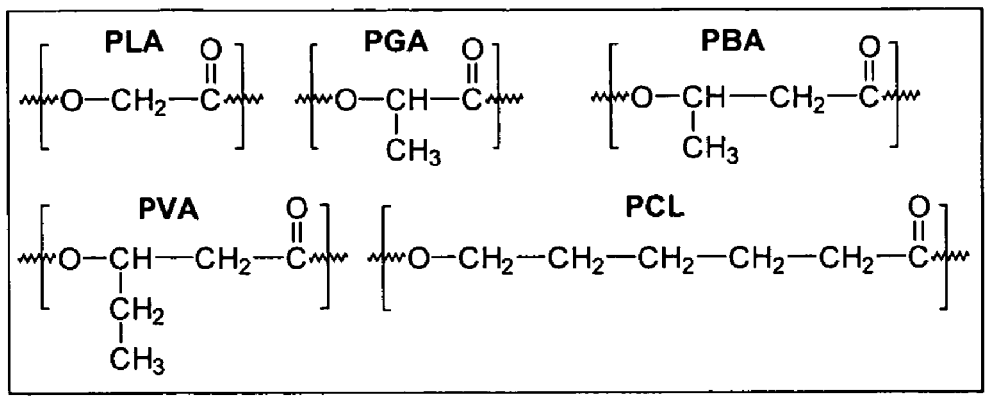
FIG. 7 depicts examples of biodegradable polyesters.
Figure 8:
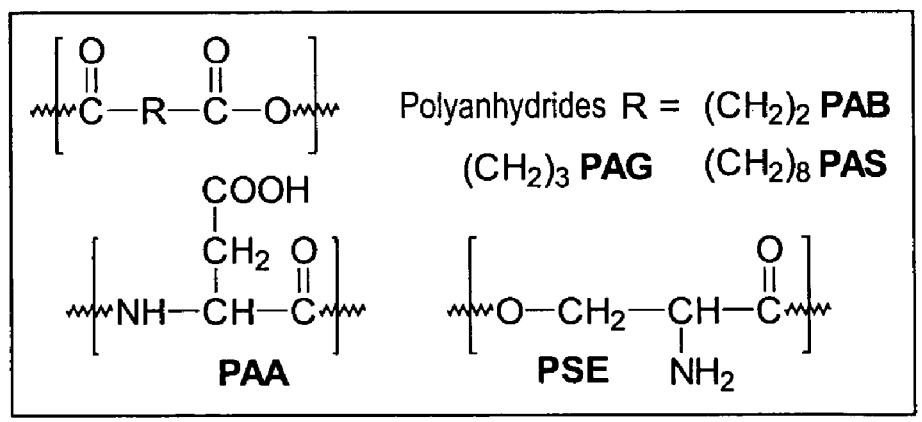
FIG. 8 depicts examples of biodegradable polyanhydrides, poly(amino acids) and polyamides.
Figure 9:
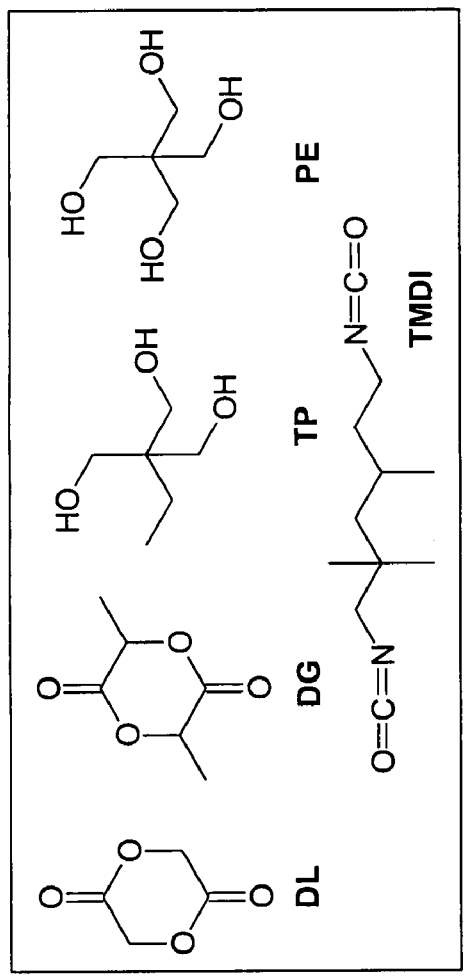
FIG. 9 depicts monomer components for amorphous polyurethane copolyester polymer networks having shape memory properties.
Figure 10:
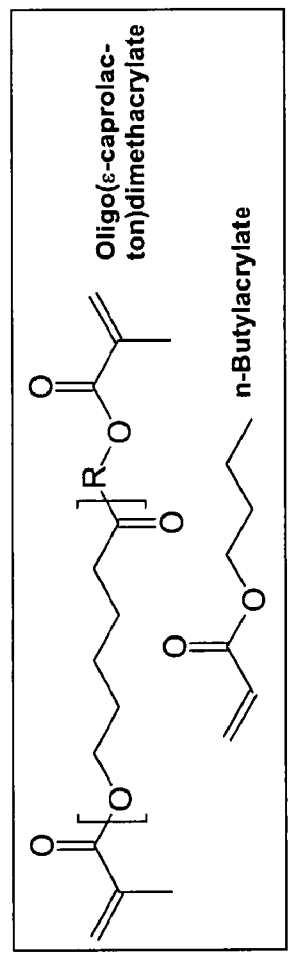
FIG. 10 depicts monomer components for covalent biodegradable networks.
Figure 11:
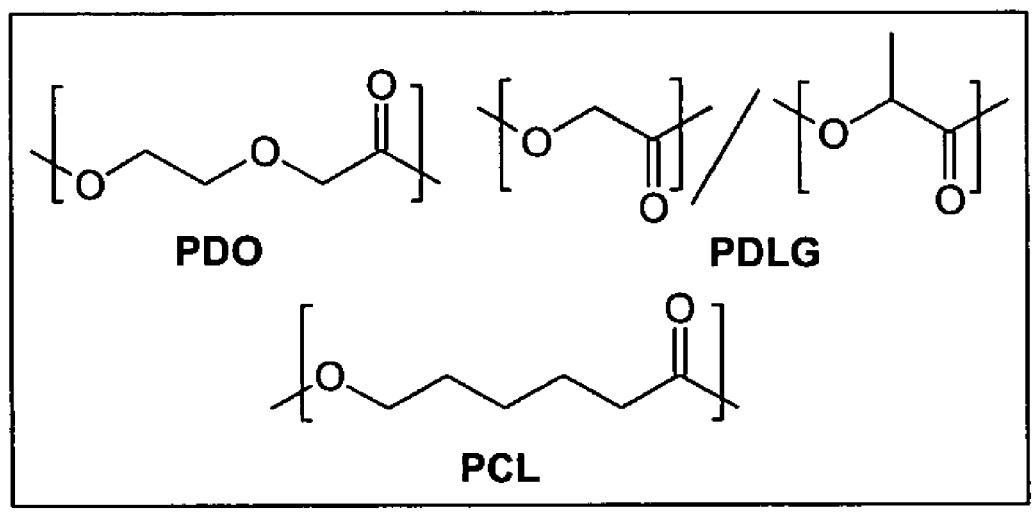
FIG. 11 depicts polymer segments in biodegradable poly (p-dioxanone)-polyurethane multiblock copolymers.
Figure 12A:
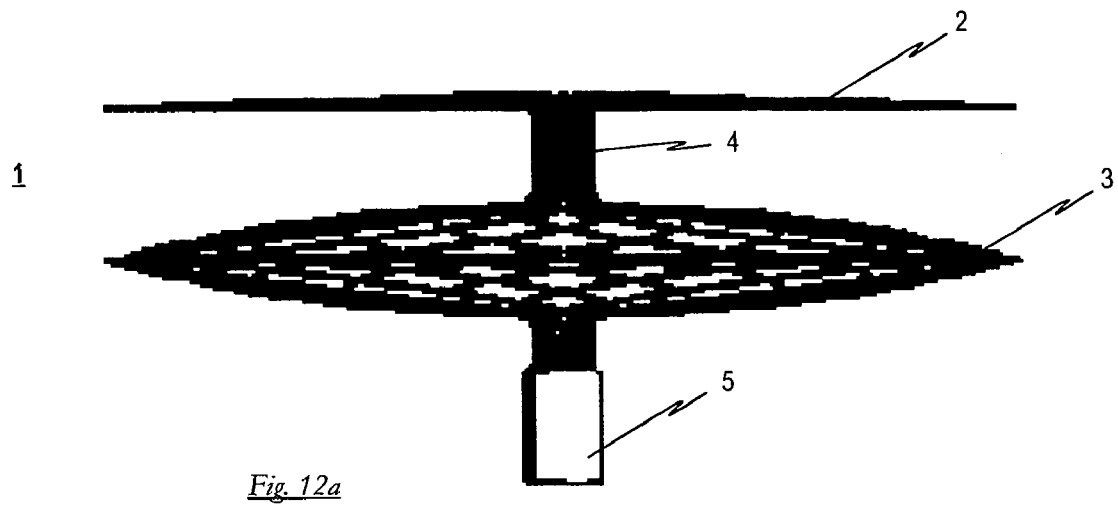
FIGS. 12*a, b* depict a side and stereoscopic view of a Type 1 PFO occlusion device.
Figure 12B:
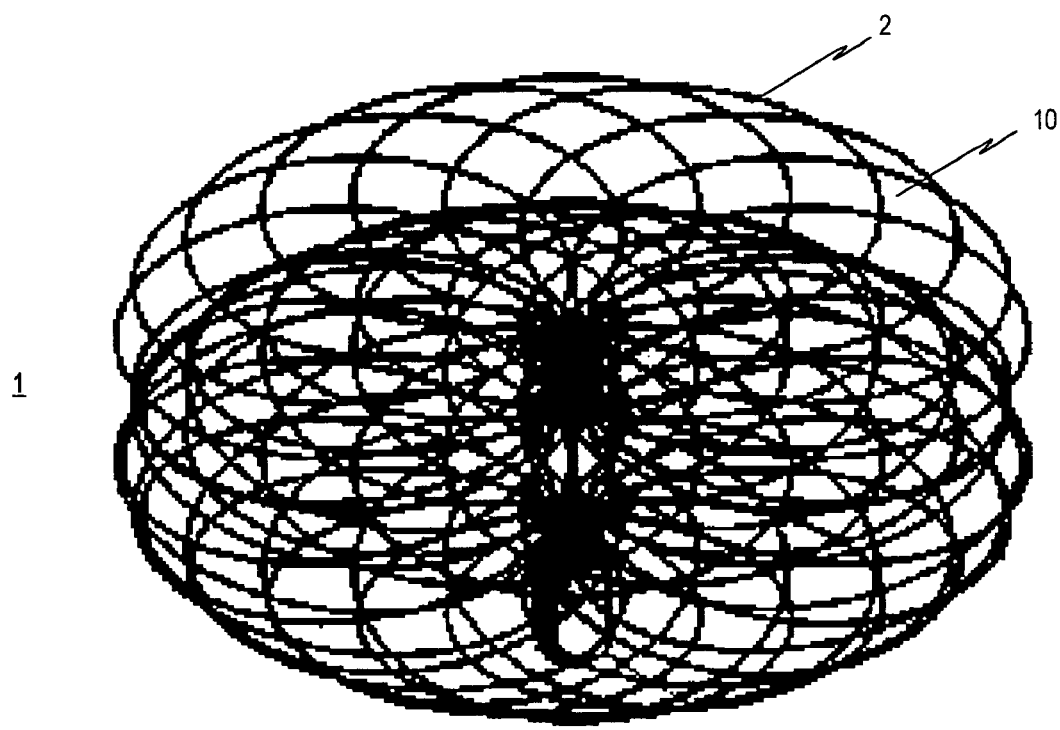
Figure 13A:
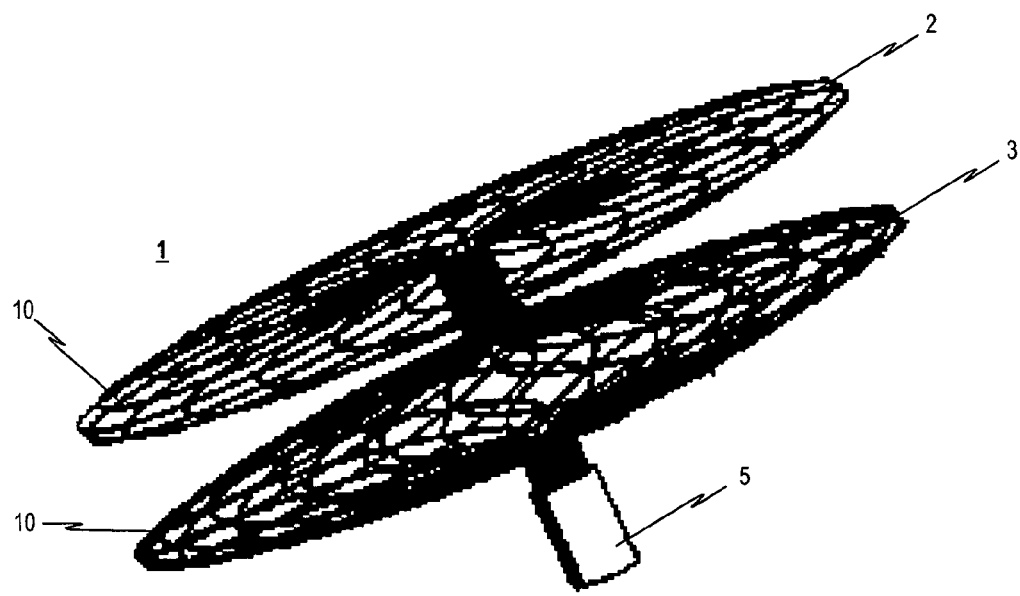
FIGS. 13*a, b* are a stereoscopic representation of a Type 1 PFO occlusion device.
Figure 13B:
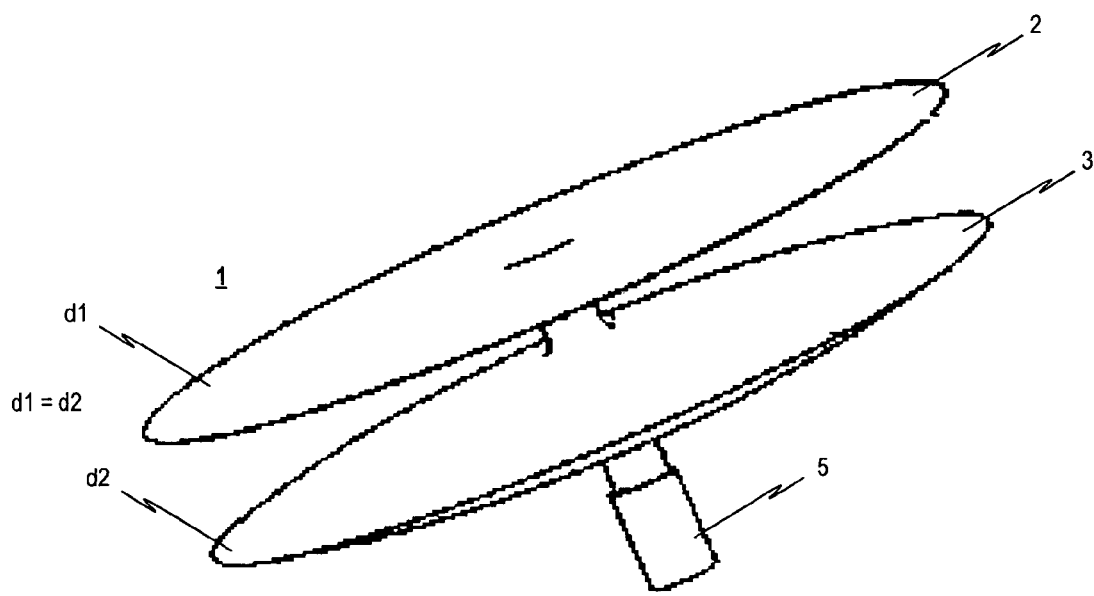
Figure 17A:
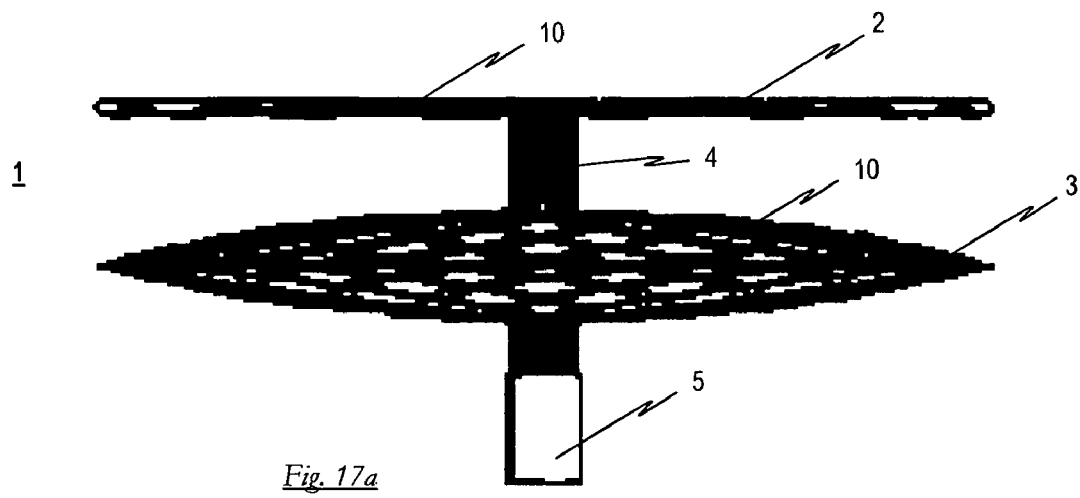
FIGS. 17*a, b* depict a conventionalized side view and sectional representation of a Type 4 PFO occlusion device.
Figure 17B:
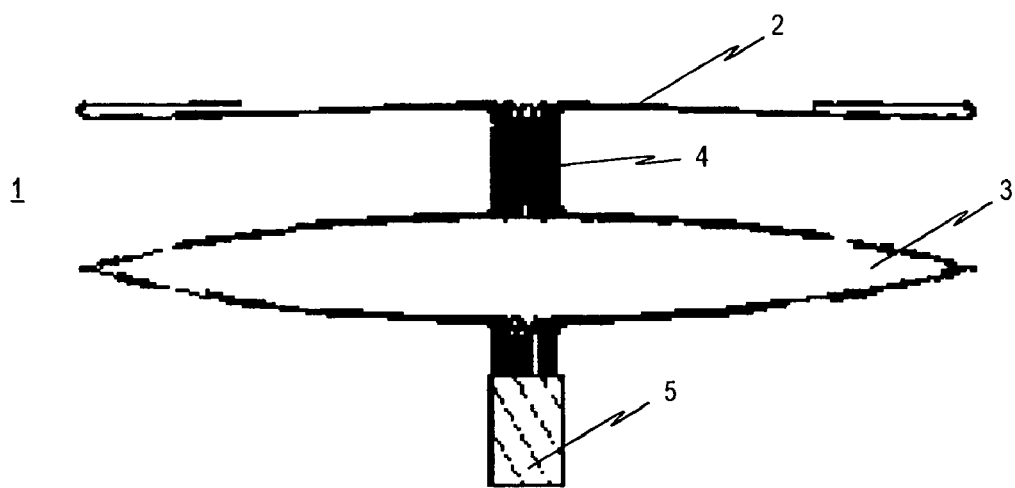
Figure 18A:
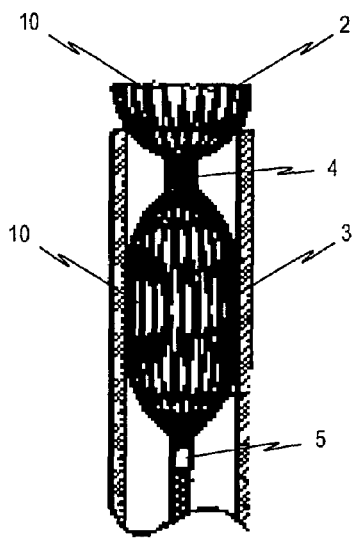
FIG. 18*a* depicts an enlarged detail view of a section as seen through a Type 1 occlusion device (Type 1 ASD occlusion device) for occluding an atrial septal defect(ASD); the occlusion device is elongated and extends partially out of the opening of an insetting catheter.
Figure 18B:
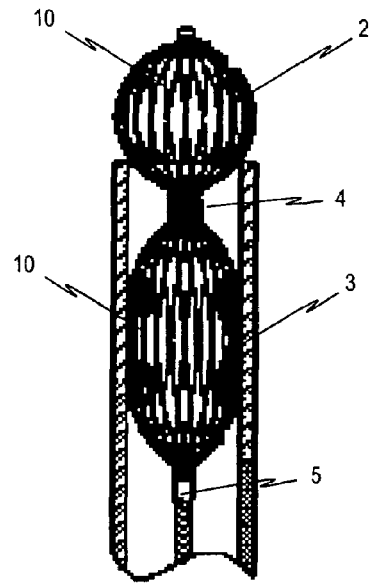
FIG. 18*b* depicts an enlarged detail view of a section as seen through a Type 2 occlusion device in a conventional embodiment.
Figure 18C:
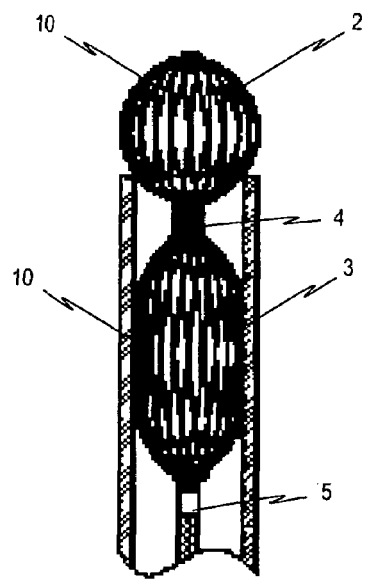
FIG. 18*c* depicts an enlarged detail view of a section as seen through a Type 3 ASD occlusion device with polymer threads thermally bundled in the left atrial curve.
Figure 18D:
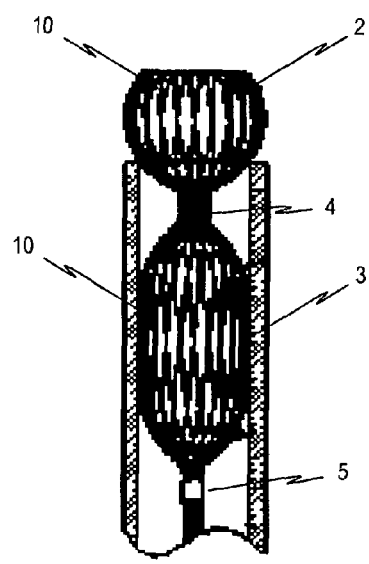
FIG. 18*d* depicts an enlarged detail view of a section as seen through a Type 4 ASD occlusion device having a type of braiding comparable to that of Type 1 (FIG. 19-21)
Figure 19A:
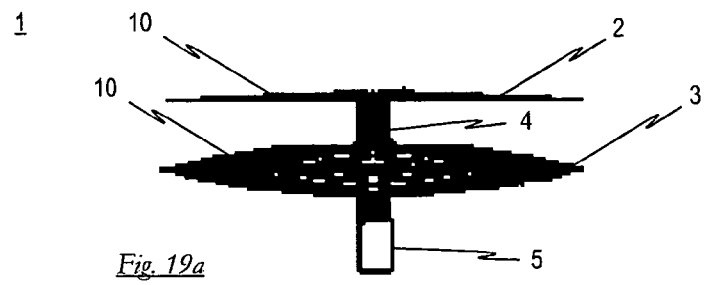
FIG. 19*a* depicts a frontal view of the Type 1 ASD occlusion device pursuant FIG. 18*a* in its pre-formed shape.
Figure 19B:
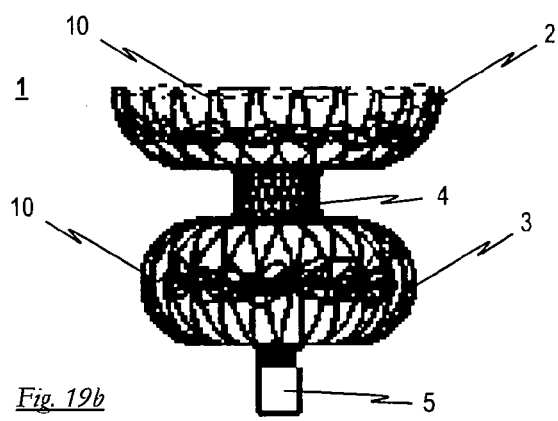
FIG. 19*b* depicts the ASD occlusion device pursuant FIG. 19*a* in slightly elongated form.
Figure 19C:
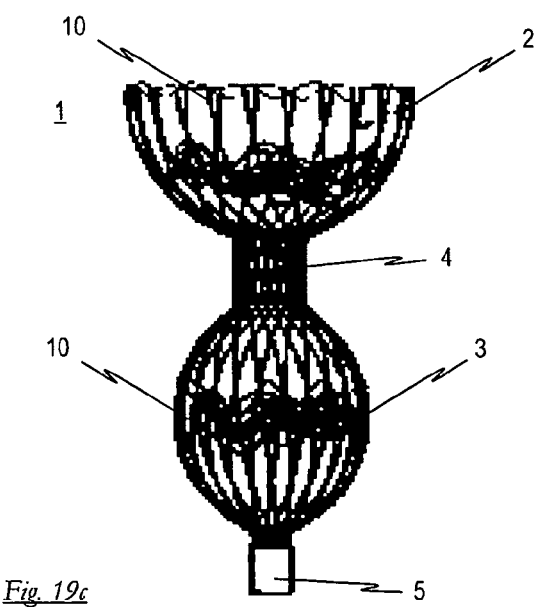
FIG. 19*c* depicts a side view of the ASD occlusion device pursuant FIG. 19*a* in further elongated form.
Figure 20A:
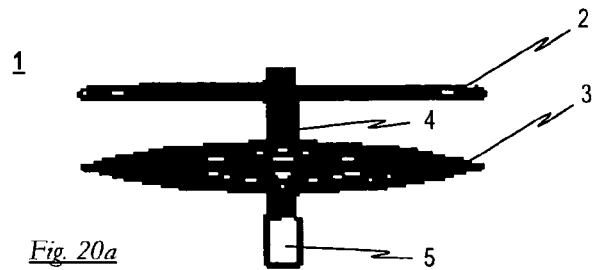
FIG. 20*a* depicts a frontal view of a Type 2 ASD occlusion device pursuant FIG. 18*b* in its pre-formed shape.
Figure 20B:
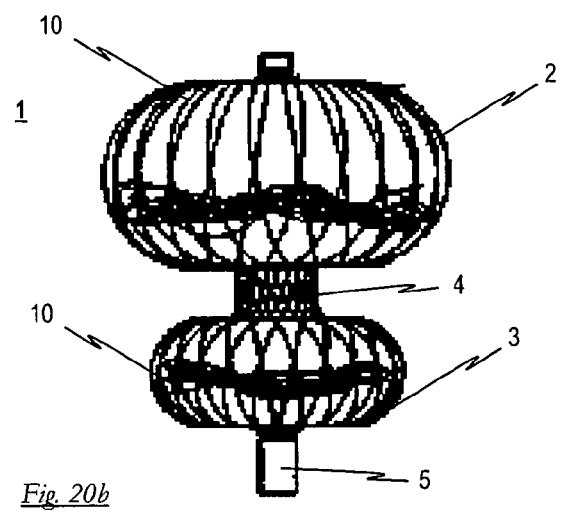
FIG. 20*b* depicts the ASD occlusion device pursuant FIG. 20*a* in slightly elongated form.
Figure 20C:
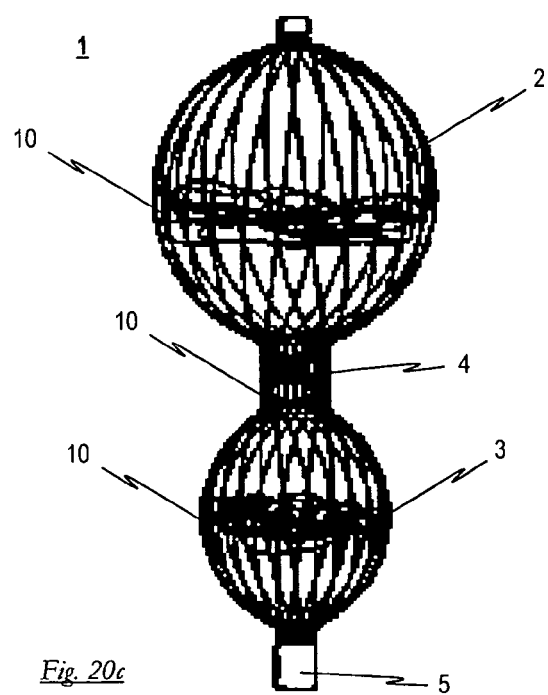
FIG. 20*c* depicts the ASD occlusion device pursuant FIG. 20*a* in further elongated form.
Figure 21A:
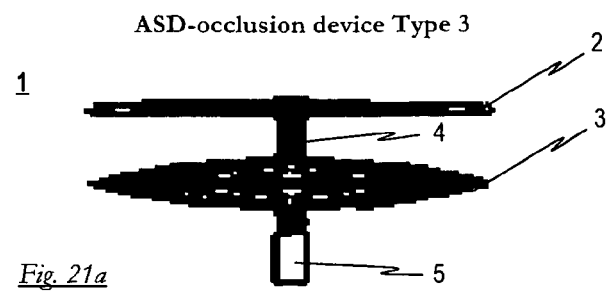
FIG. 21*a* depicts a frontal view of a Type 3 ASD occlusion device pursuant FIG. 18*c* in its pre-formed shape.
Figure 21B:
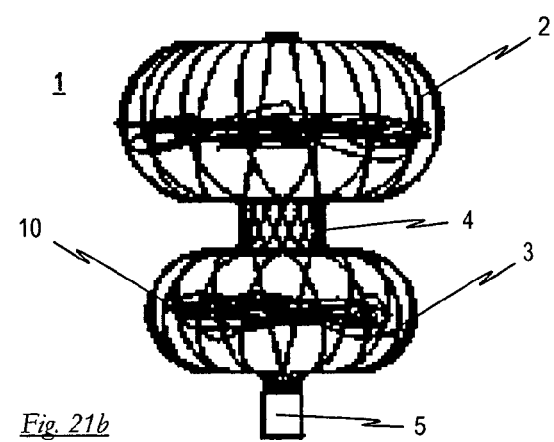
FIG. 21b depicts a side view of the ASD occlusion device pursuant FIG. 21a in slightly elongated form.
Figure 21C:
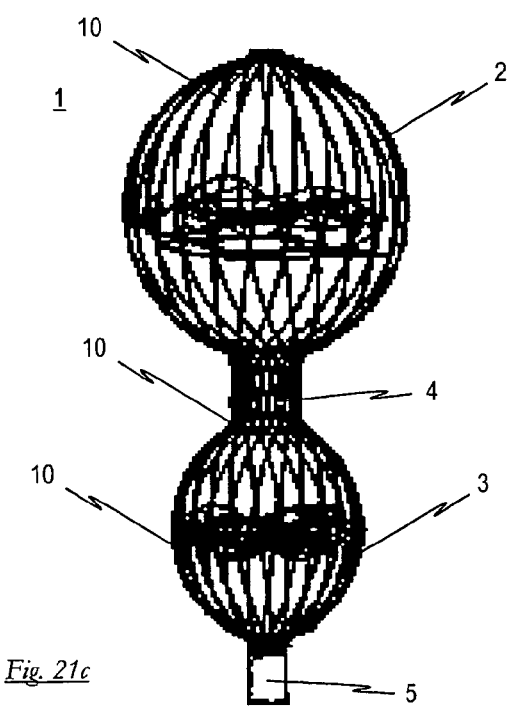
FIG. 21c depicts a side view of the ASD occlusion device pursuant FIG. 21a in further elongated form.
Figure 22A:
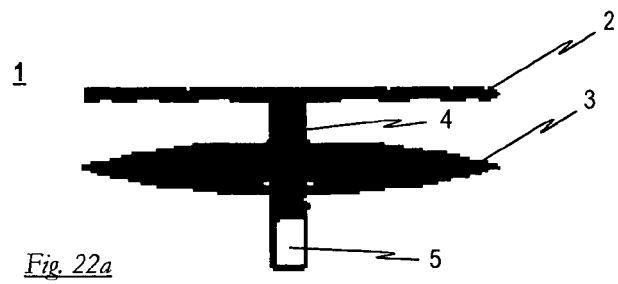
FIG. 22a depicts a frontal view of the Type 4 ASD occlusion device pursuant FIG. 18d in its pre-formed shape.
Figure 22B:
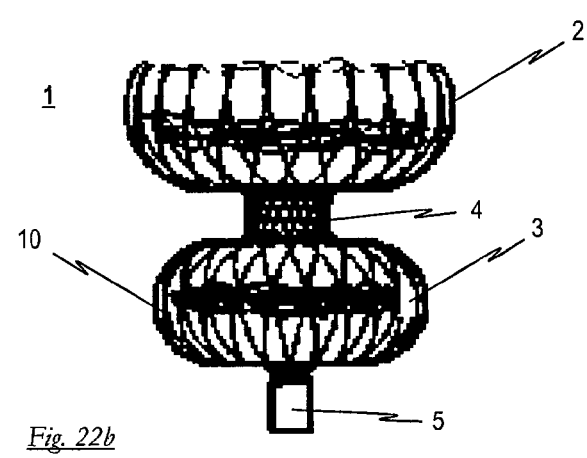
FIG. 22b depicts a side view of the ASD occlusion device pursuant FIG. 22a in slightly elongated form.
Figure 22C:
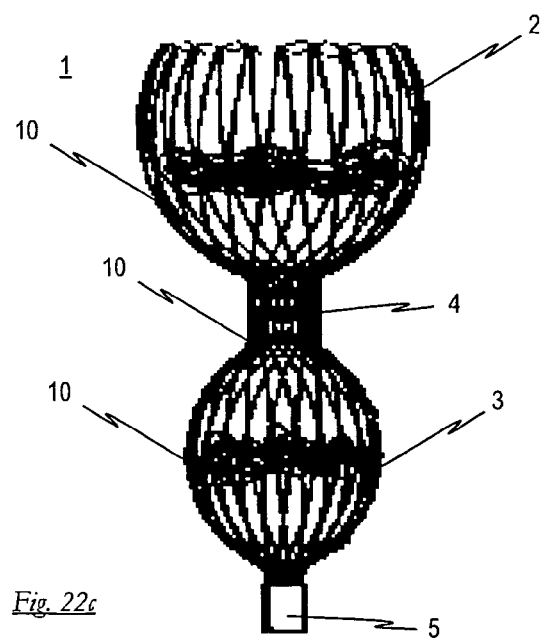
FIG. 22c depicts a side view of the ASD occlusion device pursuant FIG. 22a in slightly further elongated form.

Using the braiding method as developed by JEN.meditec GmbH in accordance with the Aug. 22, 2003 German patent application No. 10 338 702 as cited at the outset yields additional preferable forms of the device which are particularly economical in terms of material and the method used to produce such braided material enables the PFO and ASD devices to have flatter final forms. The medical devices produced with this braiding method comprise the PFO, Type 1 (FIG. 12a, b and FIG. 13a, b) and Type 4 (FIG. 17a, b) types of devices and the ASD Type 1 (FIG. 18a, FIG. 19a-19c) and Type 4 (FIG. 18d, FIG. 22a-22c) types of devices.

The pitch to the synthetic strands and the pick (i.e., the number of turns per unit length) as well as other factors such as the number of wires used in the tubular braiding are essential in defining a number of important properties for the device. The tighter the pick and the pitch of fabric 10, meaning the closer the synthetic strands are woven to one another, the more rigid the device. A greater wire density means a larger wire surface, thus increasing the device's occluding ability. Such thrombogenicity can either be increased, e.g. by coating with a thrombolytic agent, or decreased, e.g. by means of a lubricious anti-thrombogenic coating.

In the forming of device 1 in accordance with the present invention, a tubular or flat synthetic fabric 10 of corresponding size is inserted into a mold in which the fabric 10 conforms to the cavities of the mold. These cavities are configured such that the synthetic fabric 10 assumes the shape of the desired device. The ends of the synthetic strands of the tubular or flat synthetic fabric 10 should be secured in order to prevent fraying. A clamp can be used to this end (e.g. Type 2 PFO and ASD devices as described above) or the ends of the synthetic strands can be thermally treated, for example welded (e.g. Type 3 PFO and ASD devices).

In the case of a tubular braiding, a molding element can be inserted into the tube of the braiding prior to the braiding being inserted into the mold. This occasions an even more precise defining of the molded surface. When the ends of the tubular synthetic fabric have been clamped or welded, the molding element can be introduced into the tube manually by bending apart the synthetic strands of fabric 10. This type of molding element serves to provide a very precise control over the final size and shape of the device by ensuring that the fabric conforms to the cavities of the mold.

A material can be selected for the molding element which can be broken into smaller pieces or removed from the inside of the synthetic fabric. The molding element can thus, for example, be made from a brittle or friable material. After thermally treating the material with the molding element in the mold cavity, the molding element is broken into small pieces easily removed from the synthetic fabric.

Usually, however, molding tools (molding elements) can be used for all the medical devices described here which precisely define the shape of the medical devices based on an outer sleeve (fractionable into different individual pieces). Since the medical devices are made from synthetic material having a melting point below 350° C., the molding elements of the molding tool can be made of aluminum, tool steel, non-ferrous metal or even titanium or titanium alloys.

It is, however, to be pointed out that the specific form of a particular molding element will yield a specific shape and that other molding elements having other configurations can also be used as desired. If a complex shape is desired, molding elements and molds can have additional components, including cammed connections. For simpler shapes, the mold can also have fewer components. The number of components in a given mold and their shape depend almost exclusively on the shape of the desired device to which the synthetic fabric will conform. In its relaxed state, the synthetic strands of the tubular braiding assume a previously-defined orientation relative one another. When the tubular braiding is compressed along its axis, the fabric pitches away from the axis in expanding according to the shape of the mold. In deformed fabric, the relative orientation to the wire strands of the synthetic fabric changes. Compressing the mold occasions the synthetic fabric to conform to the surface of the cavity. The device has a pre-determined expanded configuration and collapsed configuration so that it can be introduced by means of a catheter or such similar inserting device. The expanded configuration is a function of the shape of the fabric after having been formed to the surface of the mold.

Once the tubular or flat synthetic fabric has been inserted into the selected mold, whereby the fabric is flush against the surface of the mold's cavity, thermal treatment then follows with fabric 10 thereby remaining in the mold. The wire strands of the synthetic fabric are re-aligned and re-formed relative one another by the thermal treatment, whereby the fabric conforms to the mold. The fabric is then removed from the mold and retains the given shape of the surface of the mold's cavity, now constituting the desired device. The thermal treatment depends to a large extent on the specific material from which the wire strands of the synthetic fabric are made, yet duration and temperature for the thermal treatment should be selected such that the fabric is fixed in its new shape; i.e., the wire strands assume their relative re-orientation subsequent the fabric conforming to the surface of the mold.

After being thermally treated, the fabric is removed from the molding element and retains its new form. In those cases where a molding element has been used, same is now removed again as described above. The duration of and temperature for the thermal treatment depends heavily on the material composition to the wire strands and has already been described in detail above.

After device 1 has been brought into the previously specified form, it can be used for treating a patient. A device is selected based on its being suitable for treating the respective medical problem. Such a device is to be consistent with one of the above-described types of application. Once the corresponding device is selected, a catheter or other inserting device is introduced into the patient and positioned such that the distal end of the inserting device positions next to the site to be treated, e.g. thus directly adjacent to (or at the same height of) a shunt of an abnormal opening in an organ.

Insertion devices can be of various shapes but should, however, preferably comprise a pliable metal shaft with threading at its distal end. The insertion device hereby serves in pushing the medical device through the tube of the catheter and positioning it in the patient. When the device is pushed out the distal end of the catheter, it is thus still being held. Not until the device is positioned within the shunt of the abnormal opening is the shaft of the catheter rotated about its axis in order to unscrew the device from the catheter.

As long as the device is still connected to the catheter, the surgeon can move the device forward and backward relative the abnormal opening until that point at which it is exactly positioned as desired within the shunt. Using a threaded clamp, as attached to the device, the surgeon can control the movement of the device out the distal end of the catheter. Once device 1 has been pushed out of the catheter, it will spring back into the expanded form it assumes in consequence of the fabric having been thermally treated. At that moment at which it springs back into its original form, it may happen that it impacts the distal end of the catheter and is thereby urged forward. This can result in an incorrect seating of the device, especially critical if same is to be positioned in a shunt between two blood vessels. The surgeon can keep hold of the device during its positioning by means of the threaded clamp; the device will not spring out uncontrollably and can be positioned accurately.

The device is collapsed and inserted into the opening of the catheter. The collapsed form of the device should be such that it can be easily inserted into the tube of the catheter and can withdraw correctly at the distal end of same. Thus an ASD occluding device can, for example, have a relatively oblong collapsed form, whereby the individual components are disposed along the axis (see FIGS. 18a-18d)). This can be attained in that one pulls the device in opposite directions along its axis by e.g. manually holding the clamps and pulling apart so that the expanded diameter segments fold inward toward the axis.

Figure 45:
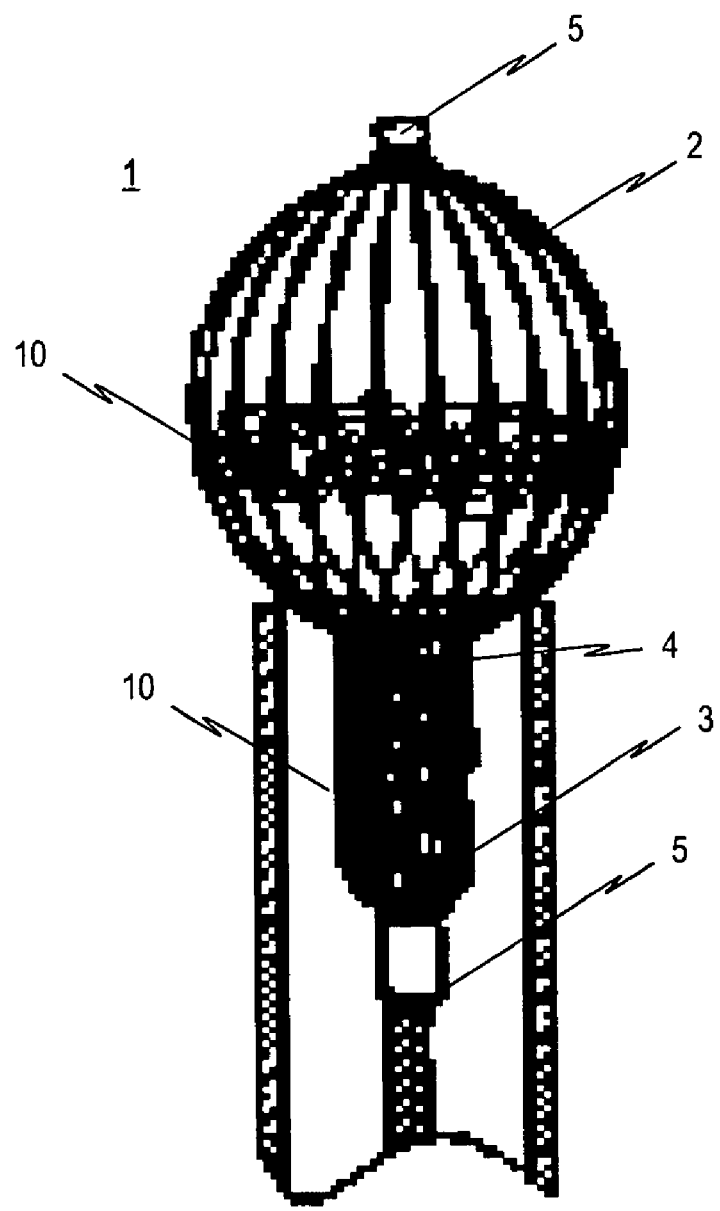
FIG. 45 depicts a PDA occlusion device within an insertion catheter.

The PDA occluding device also functions in similar fashion. It can also be collapsed to allow insertion into a catheter by stretching it along its axis (see FIG. 45), as it folds into itself when pulled in opposite directions.

If the device is to serve to permanently close a channel in a patient, the catheter is simply pulled out. The device remains in the patient's vascular system to close the blood vessel or the respective channel. In some cases, the device can be affixed to an inserting system such that the device is fixedly connected to the end of the insertion device. Before the catheter can be removed from such a system, it may be necessary to unhook the medical device from the insertion device prior to withdrawing the catheter and insertion device.

Although the device springs back into its original expanded shape (i.e., the form which it held before it was collapsed so as to enable its insertion into the catheter), it must be made clear here that it does not always assume its original shape in full measure. It can thus be desirable, for example, for the device to have a maximum outer diameter in its expanded shape which is at least as large and preferably larger than the inner diameter of the lumen of the abnormal opening at which it is to be affixed. When such a device is fit to a blood vessel or an abnormal opening having a small lumen, it expands until it fills out the lumen. When doing so, it can thereby happen that the device will not have the need to expand fully into its original expanded shape. It is nevertheless properly affixed because it shuts off the inner wall of lumen and remains fixed there.

When the device is deployed in a patient, thrombi form on the surface of the wires. In the case of greater wire density, the total surface area of the wires is increased such that the thrombotic activity at the device also increases and the blood vessel in which it is affixed closes at a relatively fast rate. Should it be desired to accelerate the occluding time, a number of thrombotic means can be disposed on the device.

The devices (occlusion devices 1) in accordance with FIGS. 12-17 are introduced in order to close defects such as the so-called patent foramen ovale (PFO). With the Type 1 to 4 PFO variants depicted here (exclusively synthetic fibers), cases of critical defects can also be treated at the locality. A detailed description of a Type 1 PFO occluder configured from nitinol material can be found in the previously-cited Aug. 22, 2003 JEN.meditec patent application Ser. No. 10/338,702.

FIGS. 18-22 show a further form of application for the present devices (occlusion devices 1), with which atrial septal defects (ASD) can be corrected. The devices (occlusion devices 1) shown in FIGS. 19-22 are a depiction of frames of the Type 1-4 ASD devices in their relaxed, unexpanded state through to partially expanded state.

ASD is a congenital anomaly of the atrial septal resulting from a structural weakness of the interatrial septum. There can be a shunt in the interatrial septum through which the blood flows from the right into the left atrium. When there is a large defect with significant shunts from left to right through the defect, the right atrium and the right ventricle overflow and the excess empties into a pulmonary vessel of low resistance.

Pulmonary vessel closure and pulmonary atrial hypertension develop in adults. Patients suffering secondary ASD with a considerable shunt (the ratio of the pulmonary blood flow to the blood flow of the system being greater than 1.5) are preferably operated on at the age of 5 or as soon as the diagnosis is made in later life. With the advent of two-dimensional echocardiography and Doppler color flow mapping, the exact anatomy of the defect can be visualized. The appropriate ASD device is selected based on the size of the defect.

The size of the ASD occluder valve is proportional to the size of the shunt to be occluded. In its relaxed state, the synthetic fabric is shaped such that two plate-like members, retention areas 2 and 3 (FIG. 19a) respectively, are in axial alignment and connected to a short cylindrical segment, or center section 4, respectively. The length of cylindrical segment 4 is to correspond to the thickness of the interatrial partition; i.e., 2 to 20 mm thick. Proximal plate 2 and distal plate 3 have an outer diameter which is much larger than the shunt so as to exclude any slippage of device 1. Proximal plate 2 is relatively flat while distal plate 3 is curved toward the proximal end such that it overlaps proximal plate 2 to some degree. Given the above, the springing open of device 1 presses the peripheral edge of distal plate 3 flush with the side wall of the septum. The outer edge of proximal plate 2 is pressed against the septum's opposite side wall in like manner.

The ends of device 1, made of metal tubular braiding fabric 10, are welded or clamped to holder 5, similar to the clamps as described above, to prevent fraying. Holder 5, which holds the wire strands together at an end, also serves in connecting the device to the inserting system (see FIG. 18). In the application as shown, the generally cylindrical holder 5 has a recess for the ends of the metal fabric so that the wires of the braided fabric 10 cannot shift relative one another. A threading is disposed in the recess of holder 5, configured such that it can receive and hold the distal end of an insertion system.

ASD occluder device 1 can be advantageously produced as a form of application for the present invention using the method specified above.

FIG. 23 depicts a detail sectional view through the side of the ASD occluder of FIG. 21 in the ASD of a heart.

FIGS. 24-28 show different variants of an occluder device, preferably used in cases of membranous VSD. In their preset form, these devices 1 have two expanded diameter sections (retention areas) 2 and 3 with a smaller diameter segment (center section) 4 disposed between said two expanded diameter sections 2 and 3. Each expanded diameter section 2 and 3 is disposed with a recess projecting inwardly from the outer surface of expanded diameter sections 2 and 3. A clamp 7 is provided in the recesses at each end of the tubular synthetic fabric 10.

The smaller diameter segment (center section) 4 has a length which corresponds to the thickness of the abnormal opening in the septum wall. The VSD device can be deformed in its expanded preset form, thereby reducing its cross-section, so that it can be introduced through a channel in the body as described above. The inner surfaces of the expanded diameter sections can be concave or curved so that the outer periphery will come into contact with each diameter section given in the septum.

At least one diameter section 2 or 3 can also be arranged to be offset relative the smaller diameter section 4. In the case of abnormal openings adjacent the aorta, this thus prevents the offset support device or the expanded diameter sections 2 and 3 from closing off the aorta after insertion.

Figure 29:
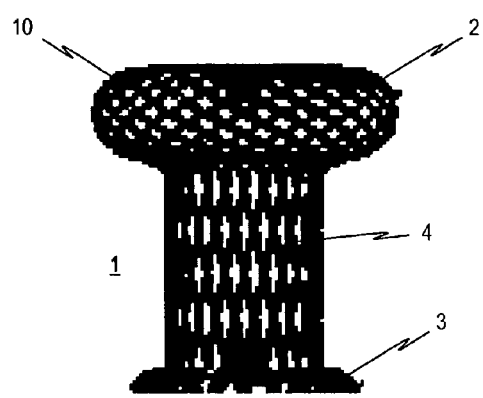
FIG. 29 depicts an enlarged frontal view of another VSD occlusion device in its pre-formed shape.
Figure 30:
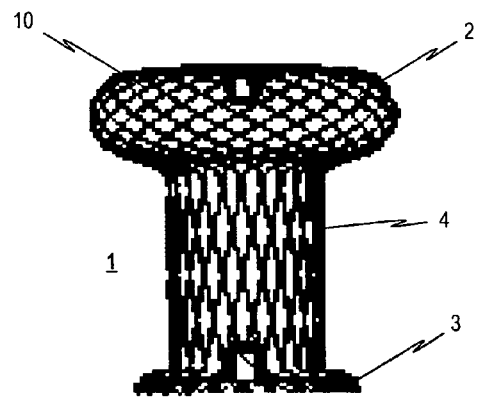
FIG. 30 depicts a detail view of a section as seen through the side of the VSD occlusion device pursuant FIG. 29.

FIGS. 29 and 30 show a VSD device 1 in which the center of both expanded diameter sections 2 and 3 and the smaller diameter section 4 are along one line. Clamps (not explicitly shown) are affixed to the ends of synthetic fabric 10 and pulled inwardly in order to yield a flat occluding device. The clamps can have an inner or outer threading for the fastening of an inserting device or guidewire. This type of VSD device 1 is preferably used to close muscular ventricular septum defects. The VSD device is inserted as described above.

Figure 31:
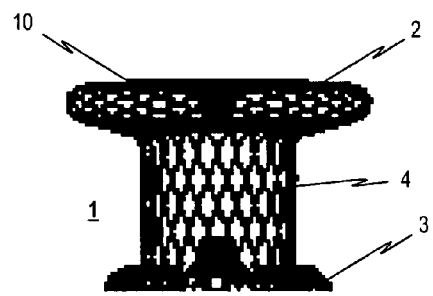
FIG. 31 depicts an enlarged frontal view of another VSD occlusion device in its pre-formed shape.
Figure 32:
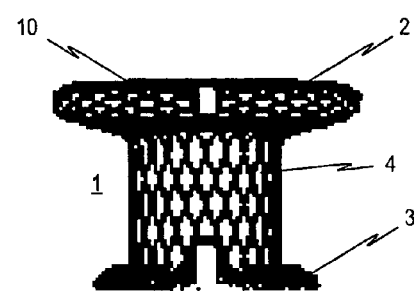
FIG. 32 depicts a detail view of a section as seen through the side of the VSD occlusion device pursuant FIG. 31.

FIGS. 31 and 32 show another form of application for device 1 in the closing of a VSD. The device pursuant FIG. 32, while similar to the VSD device of FIGS. 29 and 30, does have a few differences: the length of the smaller diameter section 4 has been reduced and both expanded diameter sections 2 and 3 have been compressed in order to reduce the thickness of each diameter section.

Figure 33:
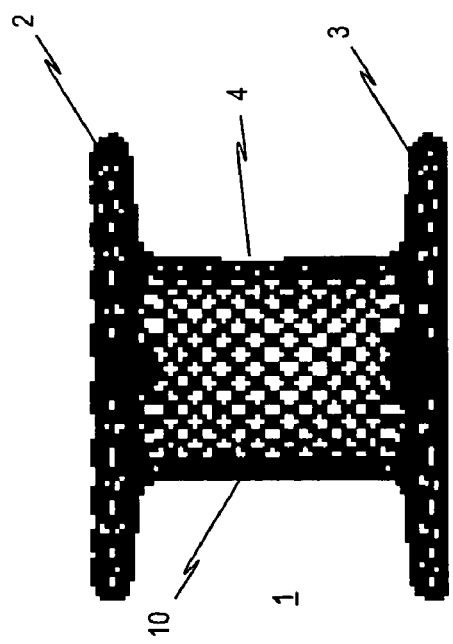
FIG. 33 depicts an enlarged frontal view of another VSD or PDA occlusion device in its pre-formed shape.
Figure 34:
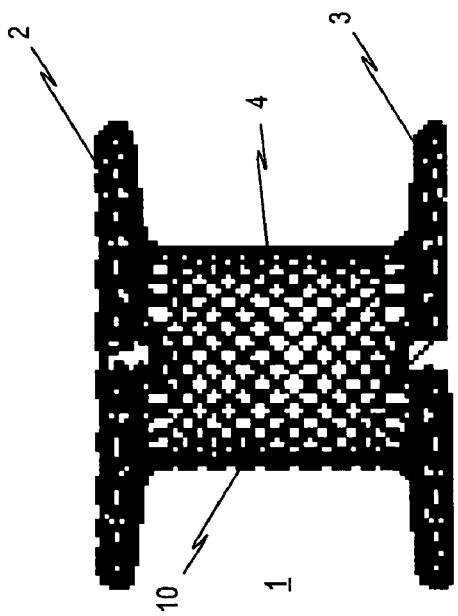
FIG. 34 depicts a detailed view of a section as seen through the side of the VSD or PDA occlusion device pursuant FIG. 33.

FIGS. 33 and 34 show another form of application for a device 1 which is similar to that as depicted in FIGS. 31 and 32. The device pursuant FIGS. 33 and 34 can occlude a patent ductus arteriosus (PDA) in which the patient is suffering from pulmonary hypertension. Both expanded diameter sections 2 and 3 are formed with a thin cross-section so as not to hinder the flow of fluid through the pulmonary vein or the aorta. In addition, the smaller diameter section 4 tapers to a point in order to increase the fabric contact area around the defect.

Figure 36:
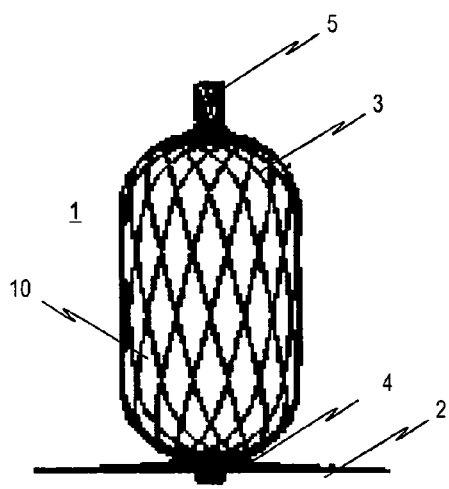
FIG. 36 depicts a side view of the occlusion device pursuant FIG. 35.
Figure 37:
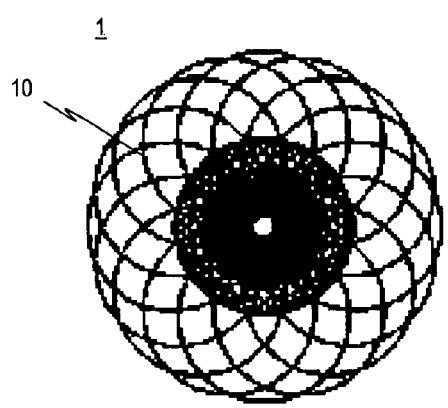
FIG. 37 depicts a top plan view of the occlusion device pursuant FIG. 35.
Figure 38:
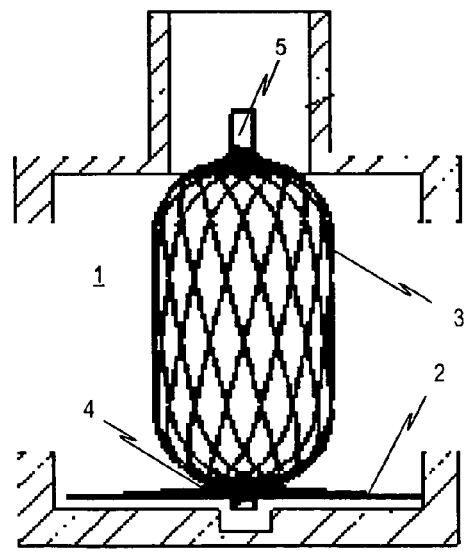
FIG. 38 depicts a partial sectional view through a molding element used for shaping the occlusion device pursuant FIG. 35.

PDA is essentially the condition in which two blood vessels, usually the aorta and the pulmonary artery near the heart, present with a shunt between their two lumen. In this condition, blood will flow from one blood vessel to the other directly through the shunt, obstructing the patient's normal bloodstream flow. The PDA device in accordance with FIG. 35 and FIGS. 36-37 has a bell-shaped body 3 and a forward section 2 projecting outwardly. The bell-shaped body 3 is adapted for affixing to the shunt between the blood vessels while the forward section 2 is adapted for positioning in the aorta in order to hold the body of the device in the shunt. The size of body 3 and end 2 can be matched to the respective size of the shunt as desired. Body 3 can thus have, e.g., in its generally thin center section, a diameter of approximately 10 mm with a length to its axis of approximately 25 mm.

The base of the PDA device body is to extend radially to the outer diameter of forward section 2, which has a diameter on an order of magnitude of approximately 20 mm.

Base 4 should have a distinct flaring in order to form the shoulder piece which tapers out radially from the center of body 3. When the PDA device is inserted into the blood vessel, this shoulder piece then abuts the edge of the lumen to be treated at high pressure. Forward section 2 is held in the blood vessel and presses against the lower end of body 3 so that the shoulder piece nestles against the vascular wall. This thus prevents the device from dislodging from within the shunt.

The PDA occluder device as a form of application of the present invention can be readily produced in accordance with the above-described method by deforming a tubular metal fabric such that it will conform to the surface of a mold; the fabric is then subject to thermal treatment in order to fix its new form.

The PDA device pursuant FIG. 39 realizes a simplification in that the use of synthetic material allows the sleeve in the proximal area since the synthetic wires are welded flush together at this location.

Figure 40:
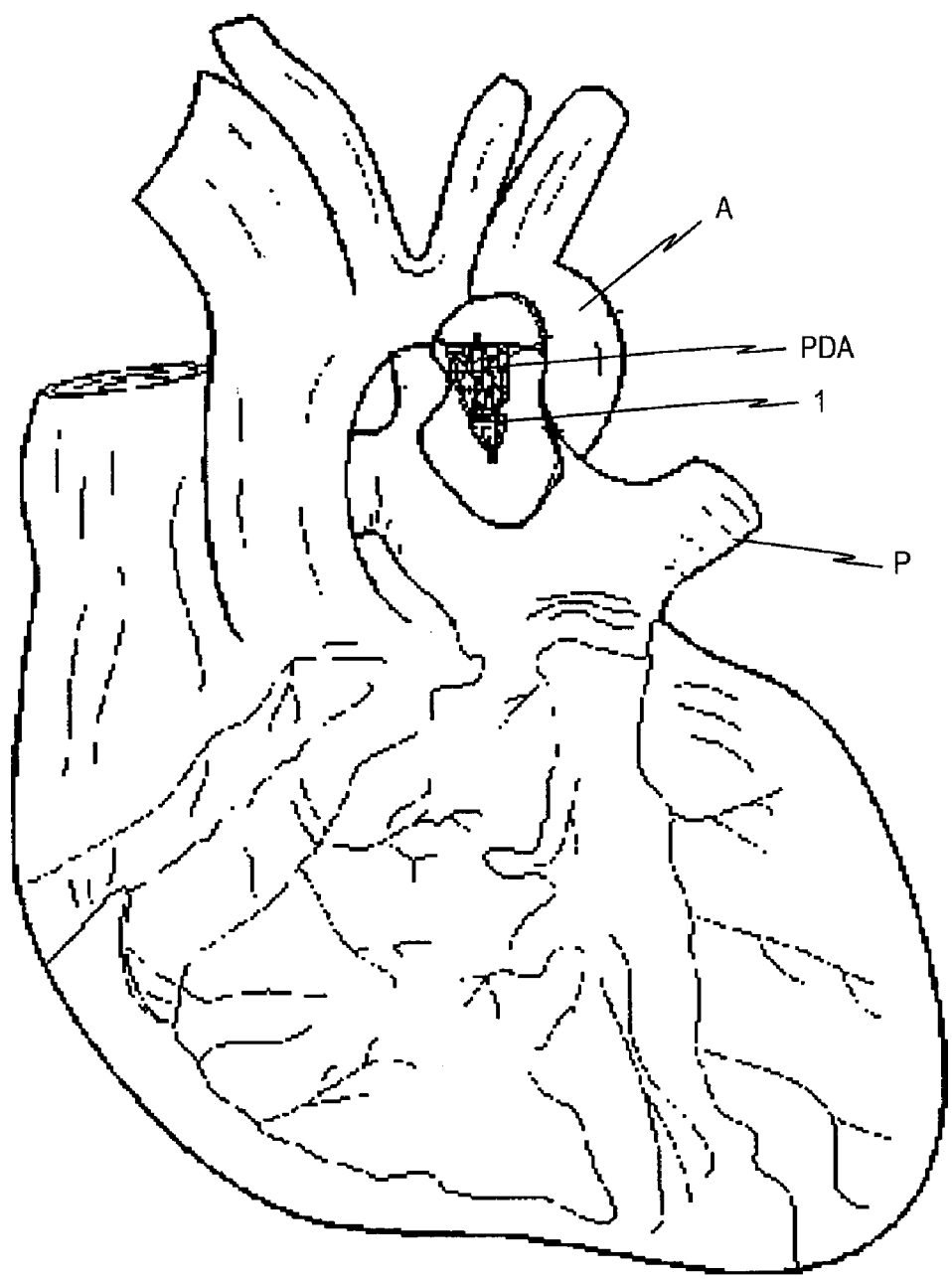
FIG. 40 depicts a perspective detail view of a section through the heart with the occlusion device pursuant FIG. 35 unfolded in a central shunt of the patient's blood vessel.

FIG. 40 is a drawing of a PDA device in the heart of a patient for the purpose of PDA occlusion. The drawing shows the device in a shunt extending from the "A" aorta to the "P" pulmonary artery. The device is guided through the PDA in collapsed state by a catheter. Subsequent thereto, the shoulder piece is allowed to spring back into its "remembered shape" as occasioned by its prior thermal treatment upon pushing the device out through the catheter's distal end. The shoulder piece should be larger than the shunt lumen of the PDA.

One then pulls somewhat on the device so that the shoulder piece affixes to the wall of the "P" pulmonary artery. If pulling continues on the catheter, the device will affix to the wall of the PDA, thereby pulling its body section 3 out of the catheter. Body section 3 can now expand. Body section 3 should be dimensioned such that it engages in the lumen of the PDA shunt by means of friction. The device is held in its place on the one hand by friction between body section 3 and the lumen of the shunt and on the other hand by the aorta's blood pressure against the shoulder piece of the device. Thrombi develop in and on the device within a short time and occlude the PDA. Occluding of the device as shown here can be even further accelerated by coating same with a thrombolytic agent, filling it with polyester fibers or a nylon material, or braiding a larger amount of wire strands together.

FIGS. 41 to 44 show another variant of the PDA device. This device has a cylindrical body 3, 4 which tapers to a point and a shoulder piece 2 extending out radially from an end of the body. The ends of the braided fabric are pressed inward in the cavity of body section 3. Clamps are thereby disposed at each end of the device's tubular fabric, by means of which the entire length of the PDA device is shortened and its manipulation is simplified.

It is emphasized that the realization of the invention is not limited to the embodiments associated with the figures, but rather can be realized in a plurality of variants without departure from the scope of the invention herein involved. It is intended that all matter contained in the above description, as shown in the accompanying drawings, the specification, and the claims shall be interpreted in an illustrative, and not limiting sense.

What is claimed is:

1. A self-expanding medical occlusion device for treating heart defects in patients, in particular closing abnormal openings in tissue, whereby the occlusion device is introduced into the body of a patient in a minimally invasive fashion using a catheter system, comprising:
    a braiding of thin threads;
    wherein said braiding exhibits a first preliminarily definable shape as the occlusion device is being inserted into the patient's body; and a second preliminarily definable shape in the implanted state of the occlusion device; and
    wherein the braiding of said occlusion device in the first profile form is in a collapsed state and the braiding in the second profile form is in expanded state; and
    wherein the threads of braiding are comprised of a shape memory polymer composite so that the braiding will deform from a temporary shape to a permanent shape by means of an external stimulus, said shape memory polymer composite comprising a linear, phase-segregated multiblock copolymer network which can exhibit at least two different phases; and
    wherein the temporary shape is given in a first profile form of braiding and the permanent shape is given in a second profile form of braiding.

2. The occlusion device in accordance with claim 1, wherein said external stimulus is a definable switching temperature.

3. The occlusion device in accordance with claim 2, wherein the switching temperature is within a range of between room temperature and the patient's body temperature.

4. The occlusion device in accordance with claim 2, wherein the polymer composite comprises polymer switching elements; and
    wherein the temporary shape of said braiding is stabilized below the definable switching temperature based on the characteristic phase transitions of polymer switching elements.

5. The occlusion device in accordance with claim 4, wherein the polymer composite exhibits a crystalline or semi-crystalline polymer network having crystalline switching segments;
    wherein the temporary shape to said braiding is fixed and stabilized by freezing the crystalline switching segments at crystallization transition; and
    wherein the switching temperature is a function of the crystallization temperature, of the switching temperature of the crystalline switching segments respectively.

6. The occlusion device in accordance with claim 4, wherein the polymer composite exhibits an amorphous polymer network having amorphous switching segments; and
    wherein the temporary shape to said braiding is fixed and stabilized by freezing of the amorphous switching segments at the switching segment glass transition;
    whereby the switching temperature is a function of the glass transition temperature of the amorphous switching segments.

7. The occlusion device in accordance with claim 1,
    wherein the first phase that can be exhibited by said linear, phase-segregated multiblock copolymer network is a hard segment-forming phase in which a plurality of hard segment-forming blocks are formed in the polymer which serve the physical crosslinking of the polymer structure and define and stabilize the permanent shape to said braiding; and
    wherein the second phase that can be exhibited by said linear, phase-segregated multiblock copolymer network is a switching segment-forming phase in which a plurality of switching segment-forming blocks are formed in the polymer which serve to fix the temporary shape of said braiding; and wherein the transition temperature from the switching segment-forming phase to the hard segment-forming phase is the switching temperature; and wherein conventional methods such as injection molding or extrusion processes can be used to set the profile form to said braiding above the transition temperature of the hard segment-forming phase.

8. The occlusion device in accordance with claim 7, wherein the polymer composite exhibits thermoplastic polyurethane elastomers of a multiblock structure; and wherein the hard segment-forming phase is formed by conversion of diisocyanates, in particular methylene-bis (4-phenylisocyanate) or hexamethylene diisocyanate, with diols, in particular 1,4-Butandiol; and wherein the switching segment-forming phase yields from oligomeric polyether/poly-esterdiols, in particular based on OH-terminated oly(tetrahydrofuran), poly(.epsilon.-caprolactone), poly(ethylene adipate), poly(ethylene glyocol) or poly(propylenglycol).

9. The occlusion device in accordance with claim 7, wherein the phase-segregated diblock copolymers of the polymer composite exhibit an amorphous A-block and a semi-crystallized B-block; and wherein the glass transition of the amorphous A-block constitutes the hard segment-forming phase; and wherein the melting temperature of the semi-crystalline B-block serves as the switching temperature for the thermal shape memory effect.

10. The occlusion device in accordance with claim 9, wherein the polymer composite has polystyrol as the amorphous A-block and poly(1,4-butadiene) as the semi-crystalline B-block.

11. The occlusion device in accordance with claim 7, wherein the polymer composite exhibits a phase-segregated triblock copolymer having a semi-crystalline central B-block and two amorphous terminal A-blocks;

wherein the A-blocks constitute the hard segment and the B-block establishes the switching temperature.

12. The occlusion device in accordance with claim 11, wherein the polymer composite exhibits semi-crystalline poly-(tetrahydrofuran) as the central B-block and amorphous poly(2-methyloxazolin) as terminal A-blocks.

13. The occlusion device in accordance with claim 1, wherein the polymer composite comprises polynorbornene, polyethylene/nylon-6-graft copolymers and/or crosslinked poly(ethylene-co-vinyl acetate) copolymers.

14. The occlusion device in accordance with claim 1, wherein the polymer composite exhibits a covalent crosslinked polymer network which is formed by polymerization, polycondensation and/or polyaddition of difunctional monomers or macromers with additive of tri or higher functional crosslinking; and wherein given an appropriate selection of the monomers, their functionality and ratio of crosslinkers, the chemical, thermal and mechanical properties of the polymer network as formed can be specifically and selectively set.

15. The occlusion device in accordance with claim 14, wherein the polymer composite is a covalent polymer network which comprises a crosslinker by crosslinking copolymerization of stearylacrylate and methacrylic acid with N,N'-methylenebisacrylamide, whereby the shape memory effect of the polymer composite is based on crystallizing stearyl-side chains.

16. The occlusion device in accordance with claim 1, wherein the polymer composite exhibits a covalent crosslinked polymer network which is formed by subsequent crosslinking of linear or branched polymers.

17. The occlusion device in accordance with claim 16, wherein crosslinking is actuated by one of ionizing radiation and by thermal fission of radical-forming groups.

18. The occlusion device in accordance with claim 1, wherein the polymer composite comprises at least one biologically degradable material.

19. The occlusion device in accordance with claim 18, wherein the polymer composite exhibits a hydrolytically degradable polymer, in particular poly(hydroxy carboxylic acids) or the corresponding copolymers.

20. The occlusion device in accordance with claim 18, wherein the polymer composite exhibits enzymatically degradable polymers.

21. The occlusion device in accordance with claim 18, wherein the polymer composite exhibits a biodegradable thermoplastic amorphous polyurethane-copolyester polymer network.

22. The occlusion device in accordance with claim 18, wherein the polymer composite exhibits biodegradable elastic polymer network, obtained from crosslinking of oligomer diols with diisocyanate.

23. The occlusion device in accordance with claim 18, wherein the polymer composite is formed as covalent networks based on oligo(.epsilon.-caprolactone)dimethacrylate and butylacrylate.

24. The occlusion device in accordance with claim 1, wherein the second preliminarily definable shape of the occlusion device is configured to close an abnormal tissue opening in a patient's heart; and wherein in its expanded state, the occlusion device exhibits a proximal retention area, a distal retention area and a center section interposed between the two;

wherein the said occlusion device exhibits a smaller diameter at the center segment than at the proximal and/or distal retention areas.

25. The occlusion device in accordance with 24, wherein the ends of the threads of said braiding converge in a holder at the distal retention area; and wherein the proximal retention area exhibits a flaring toward the proximal end.

26. The occlusion device in accordance with claim 24, wherein the center of said proximal and/or distal retention areas is offset relative the center of the center section.

27. The occlusion device in accordance with claim 24, wherein the interior of proximal and/or distal retention area exhibits a concave profile.

28. The occlusion device in accordance with claim 24, wherein the proximal retention area of said braiding extends to the proximal end in the shape of an open bell.

29. The occlusion device in accordance with claim 24, wherein the proximal retention area of said braiding extends in bell-shaped form to the proximal end.

30. The occlusion device in accordance with claim 24, wherein said occlusion device exhibits a barbell-shaped profile in its expanded state.

31. The occlusion device in accordance with claim 24, wherein said center area exhibits a smaller diameter compared to said proximal and distal retention areas; and wherein said center area exhibits a length to correspond to a thickness of an abnormal opening in a wall of tissue.

32. The occlusion device in accordance with claim 24, wherein a length of the center section is to be dimensioned such that a peripheral edge of the distal or proximal retention area overlaps the peripheral edge of the other retention area.

33. The occlusion device in accordance with claim 24, wherein the proximal and/or distal retention area exhibits a recess in which said holder is arranged.

34. The occlusion device in accordance with claim 33, wherein at least one connective element is further disposed in the recess at the proximal and/or distal retention area; and wherein said connective element can engage with a catheter.

* * * * *